(12) United States Patent
Balboni et al.

(10) Patent No.: US 8,974,543 B2
(45) Date of Patent: Mar. 10, 2015

(54) AUTOMATIC PROSTHESIS FOR ABOVE-KNEE AMPUTEES

(75) Inventors: Alessandro Balboni, Granarolo dell'Emilia (IT); Leonardo Balli, Florence (IT); Denis Mattia De Micheli, Navacchio di Cascina (IT); Gabriele Donati, Pescia (IT); Nicola Ferrini, Terricciola (IT)

(73) Assignee: Rizzoli Ortopedia S.p.A., Budrio (IT)

( * ) Notice: Subject to any disclaimer, the term of this patent is extended or adjusted under 35 U.S.C. 154(b) by 52 days.

(21) Appl. No.: 12/989,092

(22) PCT Filed: Apr. 30, 2008

(86) PCT No.: PCT/IB2008/001074
§ 371 (c)(1),
(2), (4) Date: Dec. 8, 2010

(87) PCT Pub. No.: WO2010/064063
PCT Pub. Date: Jun. 10, 2010

(65) Prior Publication Data
US 2011/0098828 A1    Apr. 28, 2011

(51) Int. Cl.
*A61F 2/68* (2006.01)
*A61F 2/66* (2006.01)
*A61F 2/50* (2006.01)
*A61F 2/70* (2006.01)
*A61F 2/74* (2006.01)
*A61F 2/76* (2006.01)

(52) U.S. Cl.
CPC .............. *A61F 2/68* (2013.01); *A61F 2/6607* (2013.01); *A61F 2002/5006* (2013.01); *A61F 2002/5033* (2013.01); *A61F 2002/6621* (2013.01); *A61F 2002/6642* (2013.01); *A61F 2002/665* (2013.01); *A61F 2002/6818* (2013.01); *A61F 2002/6836* (2013.01); *A61F 2002/701* (2013.01); *A61F 2002/702* (2013.01); *A61F 2002/704* (2013.01); *A61F 2002/745* (2013.01); *A61F 2002/748* (2013.01); *A61F 2002/7625* (2013.01); *A61F 2002/7635* (2013.01); *A61F 2002/764* (2013.01); *A61F 2002/768* (2013.01)
USPC ............................................................ 623/43

(58) Field of Classification Search
USPC ................................................. 623/24, 39–46
See application file for complete search history.

(56) References Cited

U.S. PATENT DOCUMENTS

| | | | | |
|---|---|---|---|---|
| 5,571,205 A | * | 11/1996 | James | 623/24 |
| 6,517,585 B1 | * | 2/2003 | Zahedi et al. | 623/24 |
| 6,955,692 B2 | * | 10/2005 | Grundei | 623/40 |

(Continued)

*Primary Examiner* — Bruce E Snow
(74) *Attorney, Agent, or Firm* — Ladas & Parry LLP

(57) ABSTRACT

A above knee prosthesis (P) applied to femoral connection (100) of an amputee that comprises a upper hinge (1) connected to femoral connection of the patient, an articulation axis (2) with the function of reproducing the knee movements, a tibia-calf muscle unit (3) pivotally connected to the femoral•segment and a damper (5) that reproduces some functions of the calf muscle and ensures to the prosthesis to brake and to allow the sequential swing and stance phases typical of the gait. The damper comprises a cylinder (5c) wherein a piston (10) and a stem (9) act connected to each other and adapted to carry out a damping reaction of said damper responsive to the forces loaded on the prosthesis. In particular, a force transducer is provided in the damper arranged, in particular, in the stem with a microprocessor that receives a force signal from the transducer and operates means for adjusting the reaction of the damper responsive to the detected force signal.

9 Claims, 35 Drawing Sheets

(56) References Cited

U.S. PATENT DOCUMENTS

| | | |
|---|---|---|
| 2002/0161451 A1 | 10/2002 | Biedermann et al. |
| 2004/0193286 A1 | 9/2004 | Grundei |
| 2005/0050956 A1 | 3/2005 | Gysling et al. |
| 2006/0235544 A1* | 10/2006 | Iversen et al. .................. 623/26 |
| 2006/0249315 A1 | 11/2006 | Herr et al. |
| 2007/0050044 A1 | 3/2007 | Haynes et al. |
| 2009/0187260 A1 | 7/2009 | Steiner et al. |
| 2009/0265018 A1* | 10/2009 | Goldfarb et al. ............... 623/40 |
| 2010/0138000 A1* | 6/2010 | Palmer et al. .................. 623/26 |
| 2011/0087339 A1* | 4/2011 | Pusch et al. .................... 623/43 |

* cited by examiner

Fig. 6
Fig. 6A
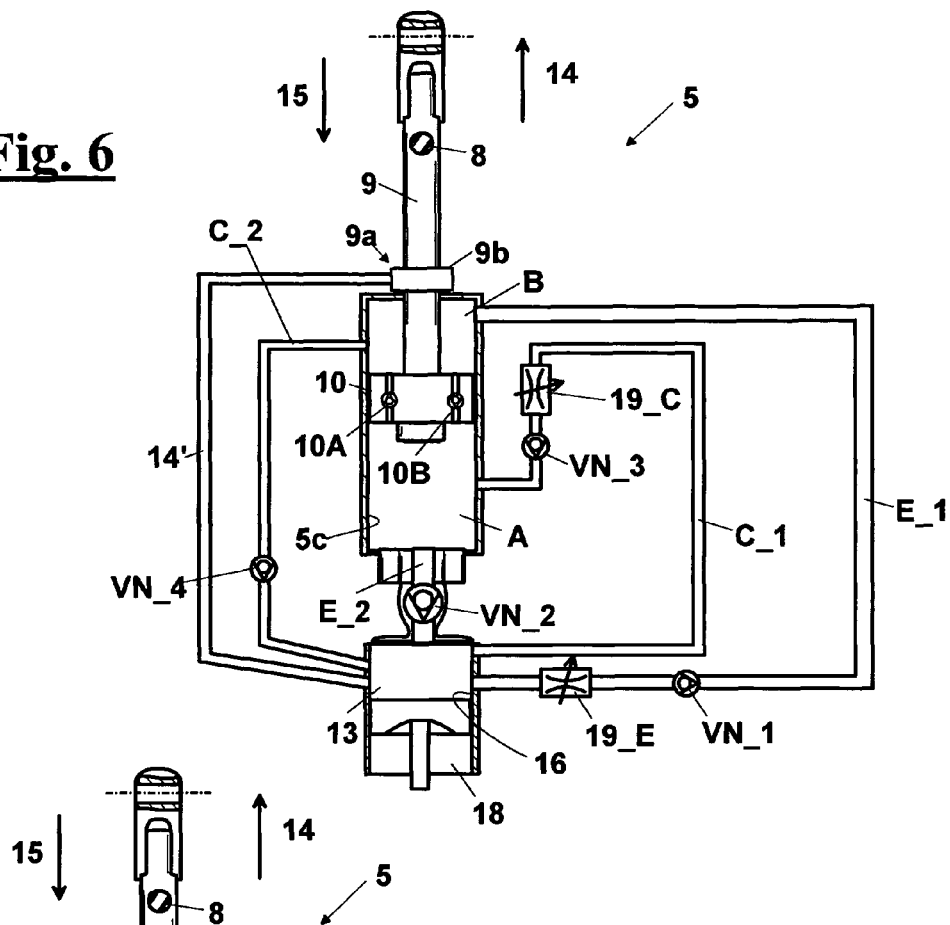
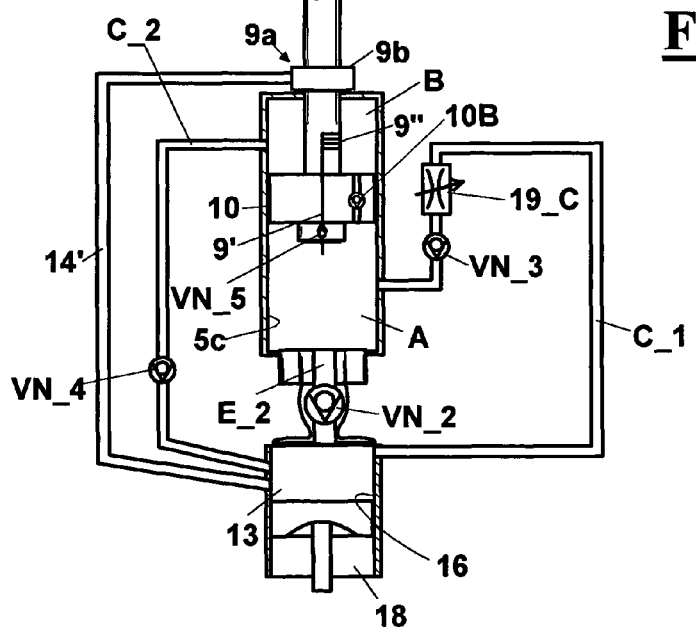

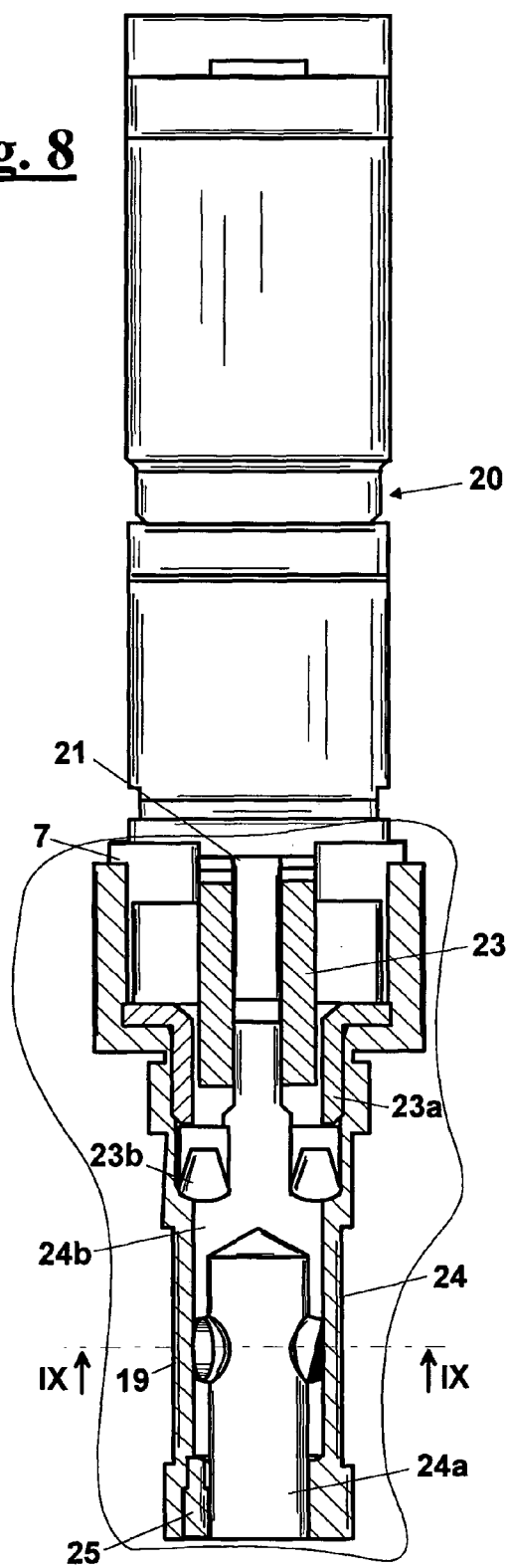
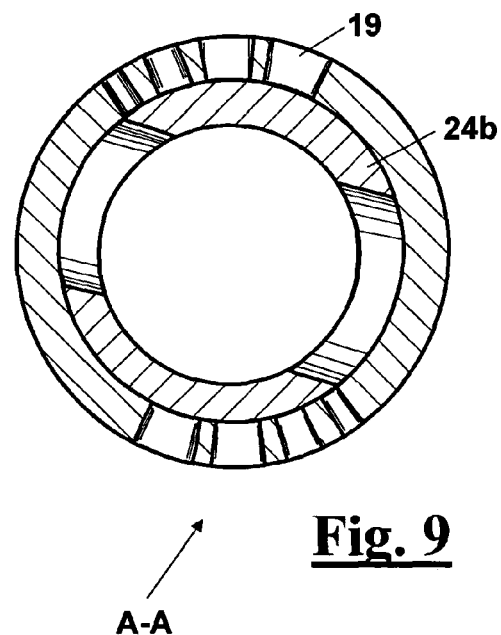
Fig. 8
Fig. 9
A-A

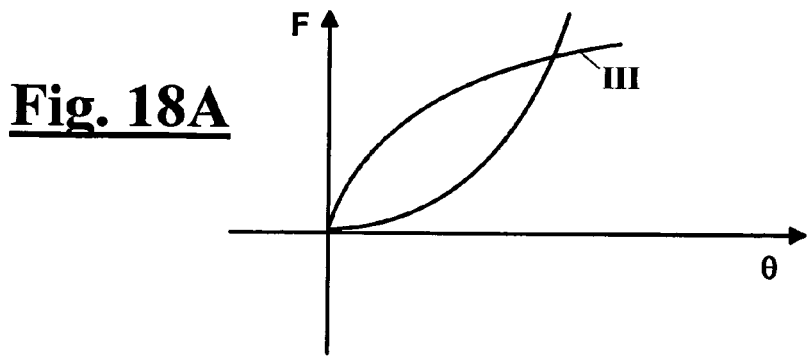
Fig. 18A
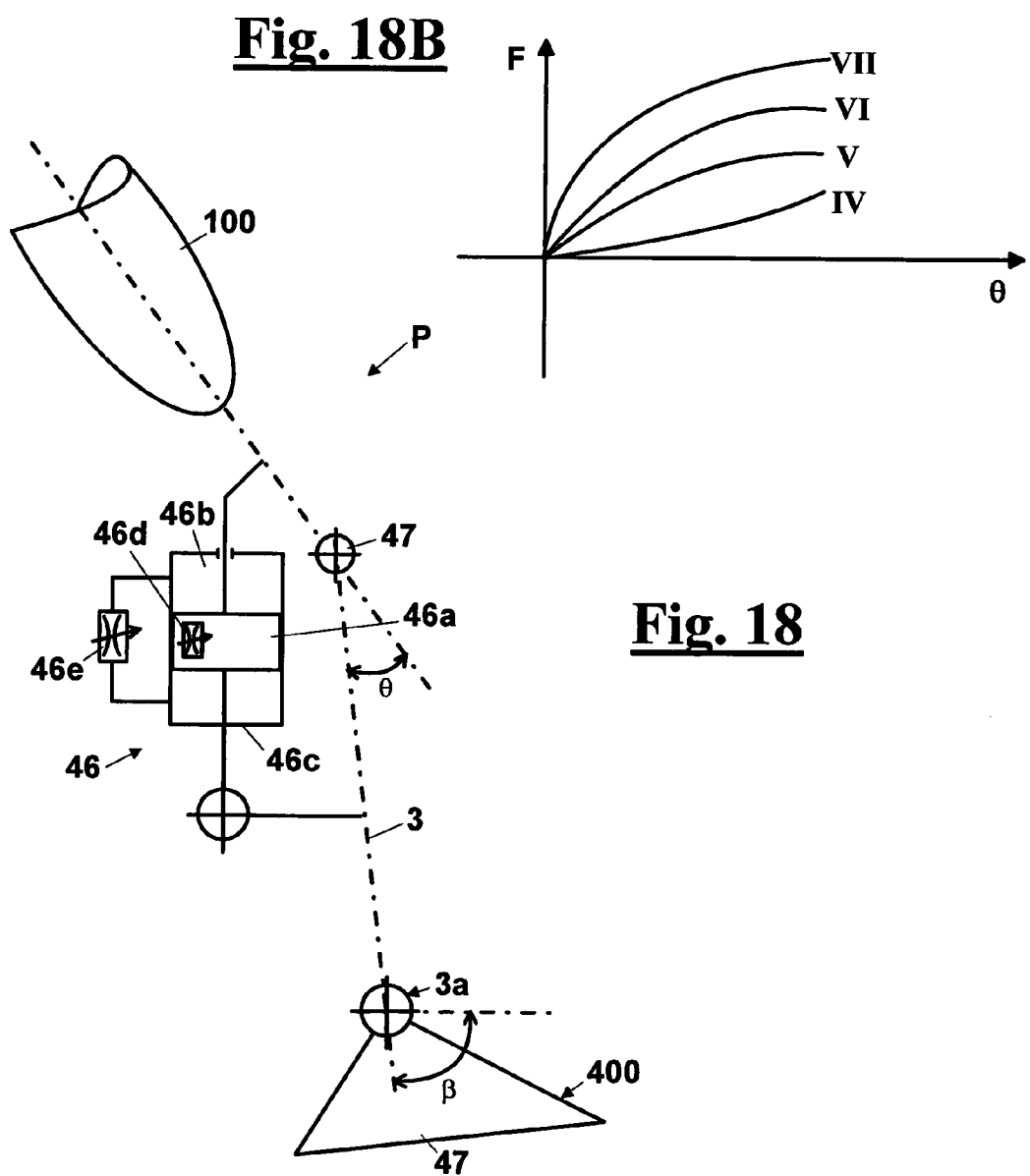
Fig. 18B
Fig. 18

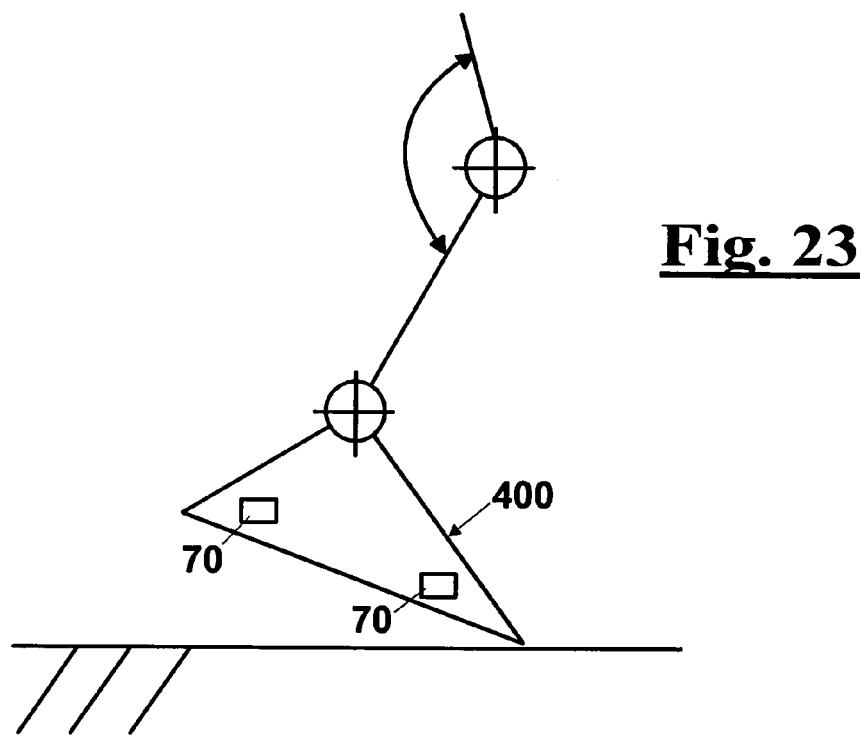
Fig. 23
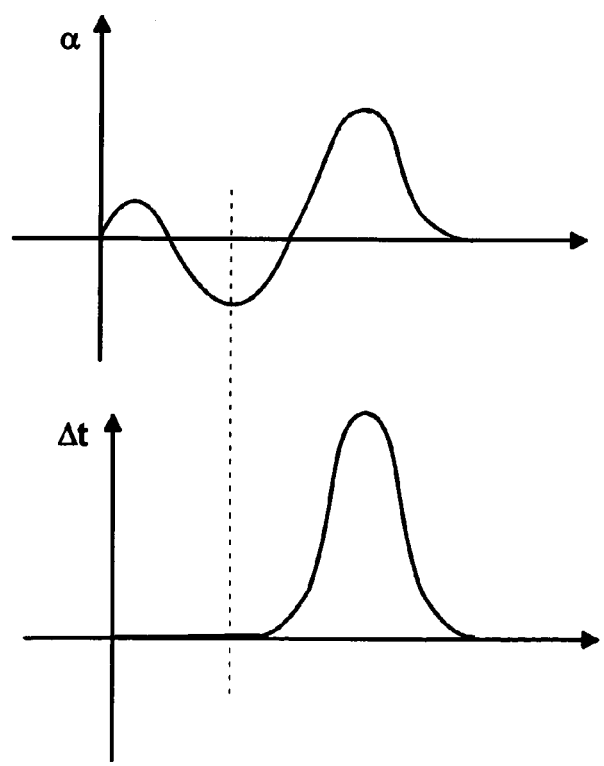
Fig. 23A
Fig. 23B

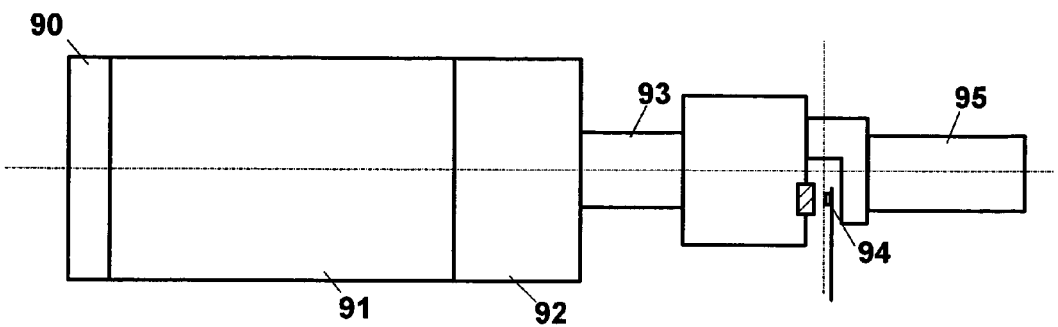
Fig. 30
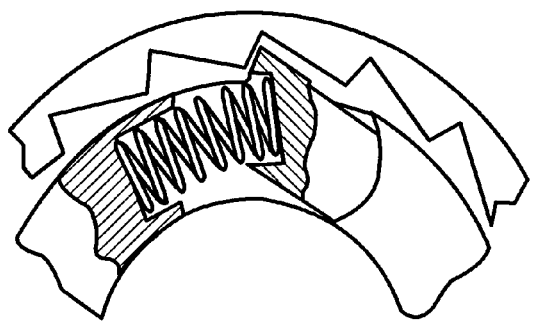
Fig. 31A
Fig. 31
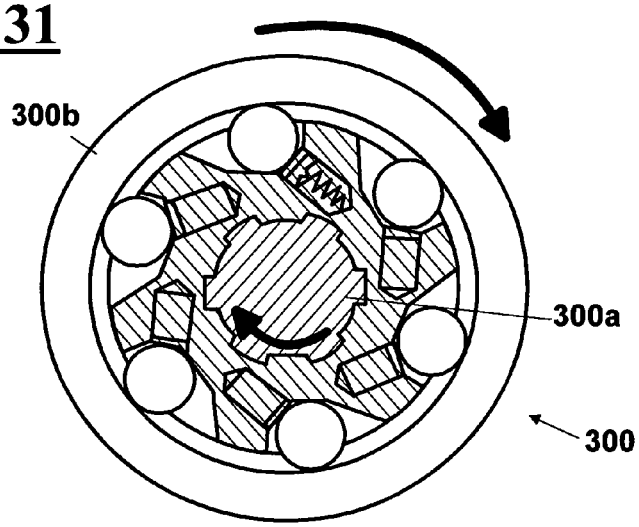

*Ing. Marco Celestino*
*ABM Agenzia Brevetti & Marchi*
*Iscritto all'albo N. 544*

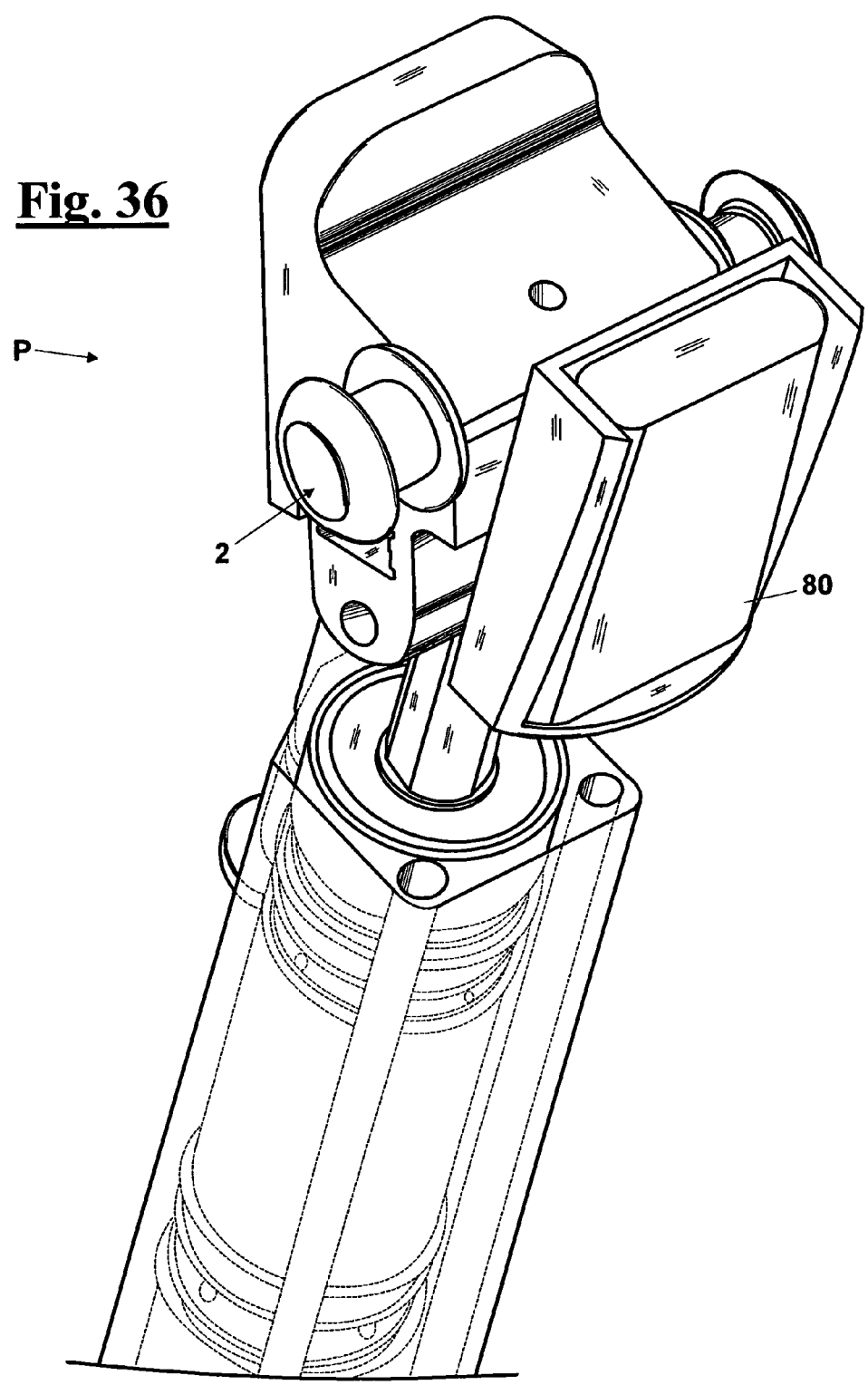

AUTOMATIC PROSTHESIS FOR ABOVE-KNEE AMPUTEES

FIELD OF THE INVENTION

The present invention relates to the field of orthopaedic appliances and more precisely it relates to an automatic prosthesis for above-knee amputees.

Furthermore, the invention relates to an electronic apparatus capable to control this prosthesis.

DESCRIPTION OF THE TECHNICAL PROBLEM

Various types are known of prostheses for above-knee amputees. In many of these types a configuration is provided with a femoral segment and a tibial segment pivotally connected to each other about an articulation axis that reproduces the knee movements. Furthermore, a hydraulic damper is provided that connects the femoral segment with the tibial segment. An example of these prostheses is disclosed in JP52047638, GB826314, U.S. Pat. No. 4,212,087, U.S. Pat. No. 3,599,245.

The tibial segment is articulated by an ankle to a foot having toes, a sole of the foot and a heel, and the knee movements can be divided into a phase so-called swing, between bringing the toes off the ground and landing the heel, and a phase so-called stance, comprising landing the heel, loading the sole of the foot and bringing the toes off the ground. By damping the relative movement of the femoral segment with the tibial segment, in the stance phase the tibial segment is braked with respect to the connection hinge between the femoral segment and the tibial segment.

In some cases, like in GB2216426, a valve with adjustable choking changes the braking action of the damper in the various steps of flexion and extension of the knee, with the adjustable valve controlled by a program and a microprocessor. GB2244006 provides also a choking cross-section through which passes the fluid of the damper. The fluid is of electrorheological type, so that when influenced by an electric field it causes the damping rate to change. A force transducer transmits data on the force acting on the leg and the microprocessor adjusts therefore the viscosity of the hydraulic damper.

Concerning the articulation axis, it can be a simple hinge, like in the above described documents, or a motor or an electromagnetic brake, like in FR2623086. The choice of the phases in which the articulation is braked or left free or, in particular, accelerated, is obtained by force transducers arranged on the tibial segment, which allows to operate the motor or the brake. Furthermore, always FR2623086 teaches to recover energy using the energy dissipated by a hydraulic pumping operated by the foot of the prosthesis, which operates a hydraulic motor located at the articulation.

One of the many problems of the existing prostheses for above-knee amputees is the risk for the toes to hit the ground during the swing phase, so-called Toe Clearance. In particular at a low speed of the gait, there is a minimum dynamic effect of the femur that is traduce in a small lifting the prosthetic foot. The stiffness of the foot same, does not assist the extension necessary between femur and tibia during the swing phase generating the risk for the toes to hit the ground during the swing phase.

Another problem, during walking on a plane ground in elder patients or in patients that are recovering the gait after above-knee amputation, is realigning the tibia with the femur. In fact, once passed the TDC between the femoral segment and the tibial segment, a difficulty arises to re-align the femoral segment and the tibial segment owing to a minimum swinging action of the tibial segment.

A further problem is the impossibility, in the existing prostheses, to adjust the pace within a gait cycle. This need is felt in situations where an unexpected obstacle is met, with need of a speed variation for passing it, or the need of stopping quickly the gait.

Yet another problem is the difficulty, for existing prostheses, to adjust the parameters of the gait progressively as the patient gets familiar with the prosthesis. Normally, it is necessary to change prosthesis or to carry out mechanical adjustments by technical experts.

Further problems are in the range of the prosthesis, which needs of battery motors or electric actuators, where present, as well as in the simplicity of the battery recharge phase.

SUMMARY OF THE INVENTION

It is an general object of the present invention to provide a prosthesis for above-knee amputees that restores the gait ability of the amputees in a way similar to that of a not disabled persons improving the prior art technique and solving the above described problems.

It is also a feature of the invention to provide an artificial limb that reproduces all the features of a missing limb, and, in particular, allows detecting data on the surroundings, and on the relative position of the limb with respect to the surrounding space.

It is another feature of the invention to provide an artificial limb that allows also detection of data on the status of the limb, in particular on the stress-strain to which the limb is subject, allowing an analysis of the instant stiffness conditions of the joints concerned with the prosthesis.

It is a further feature of the invention to provide an artificial limb that has a better logical of control with respect to the prior art, allowing to choose the operations to carry out to ensure comfort and a safe gait.

It is also a feature of the invention to provide an artificial limb that allows to supply/dissipate/recover energy during the gait at the knee joint and/or at the ankle joint, allowing in particular, to recover energy of first species (for example mechanical work) acquired during the dissipative gait phases and available to be used in the phases with a demand of energy from the limb.

It is a further feature of the invention to provide an artificial limb that allows to an above-knee amputee to perform a natural gait, with reduced energy consumption by the patient, with a reaction that is responsive to the pace, with adaptation to a variety of types of route, to minimize a request for energy from the prosthesis.

It is also a feature of the invention to provide an artificial limb to assist a patient with a very limited gait ability, i.e. elder people or patients with an unsecure gait.

Another feature of the invention is to provide an artificial limb that ensures a dynamic damping, such that comfort and steadiness are achieved during the gait avoiding unnatural stiffening reactions.

It is also a feature of the invention to provide an artificial limb that increases the safety for controlling the knee to achieve a larger clearance in the so-called Toe-Clearance phase.

A further feature of the invention is to provide an artificial limb that is adapted, through the application of suitable transducers, to determine the position of the load as the vector force with respect to the ground.

It is also a feature of the invention to provide an artificial limb that allows determining the point of application of the force from the foot to the ground as well as its intensity.

One of the objects of the invention is also to provide an artificial limb that allows perceiving and recognizing the position of the prosthesis in space and, in particular, the position of the foot with respect to the patient's body.

It is also a feature of the invention to provide an artificial limb for changing the stiffness of the knee reaction as well as it assists to avoid shocks, to recover the position of the ankle in the presence of curbs, to ensure a highly safe gait but also at avoid to the patient of have look continuously after the surroundings.

It is another feature of the invention to provide an artificial limb for changing pace of the gait within a gait cycle.

It is another feature of the invention to provide an artificial limb that increases the range of the prosthesis, by means of batteries that can be easily charged and changed.

These and other features are accomplished with one exemplary prosthesis for above-knee amputees, said prosthesis having a femoral segment, which can be fixed to a femoral connection, and a tibial segment pivotally connected to each other about an articulation axis that reproduces the knee movements, said tibial segment being articulated by an ankle to a foot having toes, a sole of the foot and a heel, wherein said knee movements comprise a phase so-called swing, between bringing the toes off the ground and landing the heel, and a phase so-called stance, comprising landing the heel, loading the sole of the foot and bringing the toes off the ground, a hydraulic damper being provided having respectively a upper hinge and a lower hinge connected respectively with said femoral segment and said tibial segment and damping the relative movement of said tibial segment with respect to said femoral segment, so that in the stance phase the tibial segment is braked with respect to the knee articulation between said femoral segment and said tibial segment, wherein the hydraulic damper comprises a cylinder-piston and a stem hinged to said piston, and microprocessor means for adjusting the damping reaction of said damper.

In a first particular aspect of the invention, the prosthesis has a force transducer in said damper, and the microprocessor receives a force signal from said force transducer and operates the means for adjusting the reaction of said damper responsive to the force signal from said damper.

In particular, said force transducer is arranged on said stem. Preferably, said force transducer is a ring dynamometer, such as a Morehouse ring, put in a hole made in said stem with axis of the hole orthogonal to the axis of the stem.

Alternatively, said force transducer on the damper is a load cell arranged at said lower hinge of said damper.

This way it is possible an instant verification of the status of load on the damper and a feedback control on the dynamic behaviour of the knee.

Advantageously, a further force transducer is provided in said femoral segment, and said microprocessor receives a force signal from said force transducer in the femoral segment operating said means for adjusting the reaction of said damper responsive to the detected force signal on said femoral segment.

In an advantageous exemplary embodiment, said force transducer in said femoral segment comprises a first force transducer adapted to measure the action on the femur according to a direction longitudinal to the femur, and a second force transducer adapted to measure the action on the femur in a direction orthogonally to the femur. This way, the overall force information on the femur and on the damper is capable of determining satisfactorily the tensional status in the artificial limb.

In an exemplary simplified embodiment, said second force transducer on the femur provides only the sign of the force on the femur in a direction orthogonally to the same.

Furthermore, a position transducer can be provided at the articulation axis that reproduces the knee movements, said position transducer measuring the rotation of the knee.

Advantageously, the femoral segment and the tibial segment is located, at the beginning of a step at the end of the swing, which is the phase of maximum extension of the movement, in a condition of singularity measured by a mechanical abutment integrated in the damper. This way, the force transducer on the damper measures the actual load transmitted to the articulation also in the condition of singularity, and the microprocessor that computes the measure can discriminate and control this step during the gait.

Advantageously, said condition of which is a condition of maximum flexion of the articulation and that normally is not part of the gait, is detected and determined by a special transducer, or by said force transducer integrated in the damper if the abutment is integrated in the damper same, so that the microprocessor can measure the full history of the loads applied to the artificial limb and, precisely, the occurrence of possible overloads that may have jeopardized the soundness of the artificial limb same, actuating, in this case, suitable signalling and emergency means.

Advantageously the damper is of hydraulic type and is characterised by blades adapted to control the oil outflow in the presence of high loads, for example shocks, assuring a high comfort to the patient.

Preferably, said damper is of hydraulic type and provides a first chamber (A) and a second chamber (B), separated by said piston, the following being also provided:
- a compensation chamber;
- a first unidirectional duct from said compensation chamber A said first chamber;
- a second unidirectional duct from said first chamber (A) to the compensation chamber along which an adjustable flow valve is located controlled by said microprocessor;
- a third unidirectional duct from said compensation chamber A said second chamber;
- a fourth duct selected from the group comprised of:
    - a unidirectional duct from the second chamber A the compensation chamber along which an adjustable flow valve is located controlled by said microprocessor;
    - a unidirectional axial duct in said stem between said second chamber and said first chamber, said stem crossing said second chamber and having a plurality of radial apertures in said second chamber such that, with the movement of said stem in said extension phase such apertures are progressively obstructed in order to provide higher resistance against the movement of said piston.

In particular, a fifth duct is provided between said compensation chamber and a oil sealing chamber on said stem, such that the pressure in said oil sealing chamber is identical to the compensation chamber, to avoid pressure peaks in the oil sealing chamber.

In a second particular aspect of the invention said prosthesis has the characteristic of being equipped with, at the foot, an insole having an array of force and position transducers whose signals are computed by said microprocessor for determining the mode of interaction of the foot of the patient with the surroundings.

In a possible embodiment of the insole the transducers located at the insole allow to determine the resultant load vector, in its intensity, direction and position components, whereby the microprocessor can adjust most favourably the reaction of the damper.

In another embodiment of the insole the transducers located at the insole provides data on the point of application of the resultant load vector, wherein one or more force transducers are provided located in the artificial limb whose signals, computed with the signal generated by said insole, allows the microprocessor to determine the transmitted resultant load vector.

Advantageously, said artificial limb comprises a further transducer of the angular position located at the ankle and adapted to control the relative inclination between tibia and foot. This information allows determining, in association to the data on the force vector provided by the insole, the position of the ankle responsive to the corresponding vector force, since necessarily the load passes through the ankle.

In a third particular aspect of the invention, said knee articulation axis comprises a generator/motor capable of providing energy in some phases of the gait cycle and of receiving energy during other phases, an energy storage unit being provided adapted to accumulate and to release again said energy through said motor operated by said microprocessor during the phases of the gait cycle.

In particular, force and position transducers are provided arranged at said knee articulation for driving the energy exchange between said energy storage unit and said generator/motor, which is therefore capable of supplying/dissipating/recovering energy. More precisely, in the microprocessor program means are resident that operate responsive to signals coming from said force and position transducers arranged according to said knee articulation, and that cause said motor/generator to work respectively as motor during a leg realignment phase and as generator during a support phase.

This way, since a large part of the gait has the knee dissipating the energy supplied by the femur in the femur-tibia relative movement, like when walking on a plane ground, there is a sensitive energy recovery by accumulating, as far as possible, the energy dissipated and releasing it back as the articulation of the leg moves when necessary. More precisely said microprocessor reduces the swinging action of the tibial segment with braking torque when landing with stabilising function. During these moments, the energy dissipated by the knee is recovered by said energy storage unit and is supplied with a variable delay in some phases of the gait cycle, in particular, when accelerating the tibia to ensure realignment with the femur. Other passive phases, for example when mechanical work is applied to the artificial limb, for example when sitting, have energy that is accumulated in storage unit.

Then, using a brake/motor device on the knee articulation, it is possible to ensure a correct arrangement of the femoral segment with respect to the tibial segment in all the gait conditions, in particular at low speed.

Advantageously, said motor acts assuring the correct realignment of the tibia if the patient, in particular, a new amputee or an elder person, has hesitations during the path.

Preferably, for reducing the energy consumption of the prosthesis, and increasing the range of the motor/generator system, variable pitch springs are provided that allow to achieve ideal stiffness, i.e. low stiffness for small angular travel between the femoral segment and the tibial segment, and high stiffness for large angular travel.

In particular, said variable pitch springs are helical springs having a diameter and a first pitch $P_1$ at one end and a second pitch $P_2$ at the other end with a continuous transition of the stiffness between a first value $K_1$ and a second value $K_2$. Alternatively, the spring is characterized by two portions having different pitch.

Advantageously, also said ankle articulation between said tibial segment and said foot comprises a motor/generator, which can be arranged in parallel to a resilient element and/or to a damping element, to force and angular position transducers connected to the microprocessor.

This way, also the ankle is adapted to brake the tibia-foot relative rotation when the heel lands, acting as generator, and to provide the power necessary to lift the foot, acting as motor.

Advantageously the motor/generator on the ankle is capable to adjust the incidence of the foot with respect to the tibial segment, allowing a much easier and natural way to avoid risks for the toes to hit the ground during the swing phase (Toe Clearance).

Owing to this feature, said prosthesis is good for amputees with low gait ability, i.e. elder people or people that hesitate during the gait, thus assisting the gait.

To avoid risk for the toes to hit the ground during the swing phase the microprocessor administers the system consisting of the motors/generators of the knee-ankle with program means adapted to recognize the phase of the gait owing to the signals coming from said force and position transducers arranged according to said ankle articulation, and to determine the risk for the toes to hit the ground during the swing phase, changing the angles of incidence of the foot with respect to the tibial segment, avoiding such risk for the toes to hit the ground during the swing phase. Thus, the knee-ankle system is adaptive with respect to the evolution of the gait of the patient assuring a better and safer performance.

Advantageously, the knee and the ankle share a same energy storage unit; therefore when the motor/generator connected to the knee must work as motor it can use the energy accumulated in the energy storage unit, previously generated by the motor/generator connected to the ankle in the phases where the latter has worked as generator.

An application of this concept is to go up the stairs: the foot rests a step, and the movement forward of the barycentre produces a work on the ankle that can be accumulated, this energy is then used as a contribution the knee for lifting the patient's body. This way, the knee and the ankle are interfaced with each other and exchange energy through said energy storage unit to accomplish a total energy recovery (Total Recovery System).

Advantageously the motor/generator devices that are associated to the joints of the knee and of the ankle and the energy accumulator are fluidic devices.

In a fourth particular aspect of the invention, the artificial limb comprises means adapted to adjust the pace of the gait in a same gait cycle, said means providing functions at least of the following variables: time, relative rotation angle between tibia and femur, and first derivative with respect to time for said angle.

In particular, said means adapted to adjust the pace of the gait in a same gait cycle comprises closed curves. Walking on a plane ground, for example, is defined by a family of similar curves having different amplitude responsive to the average walking speed. More precisely, said means adapted to adjust the pace of the gait in a same gait cycle provides defining the curves in a n-dimensional space adapted to describing a gait cycle, said curves consisting of the trajectory of the tibia with respect to time described by the angle tibia-femur and by its derivatives with respect to time.

In case of walking on a plane ground each curve defines an ideal gait cycle for a determined average speed, such that as the average speed changes the curve changes its amplitude, but the curve shape is substantially the same. Then a family of similar curves, described in a plane or a multidimensional space, identifies univocally walking on a plane ground and a parameter, such as the average speed, discriminates the curves of the family from one another.

Means are provided for measuring changes of the speed in a gait cycle and means for causing the tibia to follow a corresponding curve in that phase of the gait cycle. This way, it is possible to recognize quickly the need of the amputee to change the speed of the gait, and then to switch the tibia to follow a curve of different amplitude with respect to the previously followed curve without awaiting the beginning of the successive cycle.

The typical operations of stopping from walking, sitting down and standing up can be defined in turn by special families of curves. Similarly, walking uphill, downhill, going down and up the stairs, pedaling on a bicycle, skiing, and substantially any other possible gait types, can be represented, in general, in a n-dimensional space, by families of characteristic curves.

Each family of curves is characterized by one characteristic shape and by parameters that label them to distinguish them with respect to other curves.

In a possible configuration, exemplifying and not limitative, in said space the coordinates are five:
  time;
  relative rotation angle between tibia and femur;
  first derivative with respect to time for said angle;
  algebraic value of the resultant load vector transmitted to the ground;
  algebraic value of the moment of said resultant vector with respect to the axis of rotation of the articulation.

It is possible to put further parameters, such as the second derivative of the angle, for representing in a more complete and generalized way the different possible gait conditions.

In a preferred simplified configuration the coordinates of the space are three: tibia-femur rotation angle, first derivative with respect to time for the tibia-femur rotation angle, force acting on the damper.

Transducer means are further provided adapted to measure continuously with respect to time, or at discrete time intervals, the parameters that represent the coordinates of said space. In particular, at least one memory unit is provided, such as a RAM, ROM, EPROM etc. adapted to memorize the characteristic data of said curves and to memorize the data determined by the transducers with respect to time.

Furthermore, a microprocessor is provided adapted to analyse the data determined by the transducers, comparing them with the data recorded in said memory unit, for determining, among the recorded data, the family of curves and the curve that is most suitable for representing the actual gate, called ideal curve.

Said microprocessor adjusts the reaction of the damper for minimize errors, for example distance errors, in n-dimensional space, between the actual point, whose coordinates are defined by the measurements made by the transducers in the actual instant, and the corresponding point of the ideal curve as well as force errors under the angle an the derivative of the angle of the articulation (knee or ankle).

Advantageously, said microprocessor ascertains, according to the error, to the ideal curve used and to the family of curves, if it is useful to continue on the actual ideal curve, or if it is better to use a different ideal curve or to change family of curves.

Advantageously, said architecture of control is adapted to optimize the gait responsive to the evolution of the psycho-physical conditions of the patient, therefore the patient walks always at best both just after the amputation, when hesitation for the gait is high, and when the amputee has acquired more confidence. A further advantage is that the time for rehabilitation is reduced, since the patient is continuously assisted by a device that carries out the function of electronic rehabilitating device suitable for correcting and improving the gait.

A possible exemplary embodiment provides measuring the moment of the femur at the articulation, and in this case, without limiting the scope of the invention, the coordinates of said space are the following:
  time;
  relative rotation angle between tibia and femur;
  first derivative with respect to time for said angle;
  longitudinal force acting on the damper;
  moment transmitted by the femur to the articulation.

The latter parameter allows detecting indirectly the wishes of the patient because these are evidenced by the moment that the stump produces on the articulation.

Without limiting the scope of the invention the need of accelerating the gait on a plane ground causes a variation of moment and/or force orthogonally to the femur, and a situation similar occurs when the patient wishes to decelerate.

The control system, acquiring the values of these parameters that are correlated to the need of the patient, is capable to adjust the behaviour of the artificial limb to ensure a very quick response to follow instantly the wishes of the patient. Said control system is suitable especially for those patients that need a high dynamism. In general it recovers, at least partially, proprioception of the missing limb, since a direct relationship is established between wishes of the patient, for example the pressure of the stump on the prosthesis, action and perception.

Alternatively, said means for defining the gait conditions are of matrix type.

In a fifth particular aspect of the invention, a reduction gear is provided having a fast shaft connected to an electric motor and a slow shaft connected to the knee articulation, being the motor fed by a current, whose intensity is adjusted by a microprocessor to obtain a reaction torque at the articulation axis similar to that obtainable by a hydraulic damper.

Advantageously a second gear motor is provided connected to the ankle articulation controlled by the microprocessor, in order to obtain a reaction torque similar to a hydraulic damper.

Advantageously said reduction gear, located at said knee articulation, has a fast shaft connected to an electric motor and a slow shaft connected to the articulation that are orthogonal to each other, to achieve a reduced encumbrance as far as possible similar to the anatomic sizes.

Advantageously the artificial limb provides a second gear motor having orthogonal axes connected to the slow shaft at the ankle articulation.

Preferably, said gear motor, in particular a worm drive, has a gear ratio between said fast shaft and said slow shaft that is higher or equal to 5, on said fast shaft being mounted a first position transducer to know the instant position of said fast shaft; on said slow shaft being mounted a second position transducer, said motor piloting said fast shaft in order to maintain a predetermined play with said slow shaft and to allow the reversibility of the motion.

Advantageously between said reduction gear, located at said knee articulation, and said articulation is located a freewheel adapted to free the tibia from the reduction gear during the swing phase, i.e. caused by the inertia of the leg, vice-versa the freewheel constrains the two movements to each other when the motor/brake has to act on the tibia.

Alternatively to said freewheel, on said shafts of the reduction gear two angular transducers are applied adapted to measure the angular position of said shafts.

Since said reduction gear is characterised by an efficiency of retrograde motion less than the efficiency of the direct movement, said microprocessor computes the data produced by said transducers and operates the motor for keeping the contact between the teeth of the gears opposite to the transmission side of the retrograde torque, to limit the dissipation in the reduction gear of the kinetic energy of the leg; this may take place owing to the unavoidable backlash present in the kinematical chain that, in this case, has a positive role allowing to the microprocessor to operate the motor in order not to brake, or to brake the least possible, the inertial energy of the leg.

In an alternative exemplary embodiment, one or more moment transducers are provided instead of the angular transducers; in this case the microprocessor operates the motor managing the amount of power that has to be dissipated on the gear motor and/or has to be stored the accumulator.

In a sixth particular aspect of the invention, the electronic devices that are arranged in the artificial limb, both in the case of only the knee articulation and in the case of the latter in combination with the ankle articulation, are fed by a rechargeable battery, for example of the type with lithium ions, replaceable quickly and autonomously by the same patient that can wear the artificial limb when replacing the batteries.

A special device, for example an acoustic alarm, signals to the patient when the battery on the artificial limb is going to be flat, and the patient can easily replace it with a second battery that has been brought with; this way, the range of the prosthesis is longer.

The number of charged batteries that the patient carries with can be naturally larger than two, and this is advantageous for patients who like trekking, or who are accommodated, even occasionally, where electricity is not easily available, or to avoid long waits for one battery to be recharged.

Alternatively, on the artificial limb a USB port is present, in an exemplifying and not limitative way, by means of which the artificial limb can be connected, both in the case of only the knee articulation and in the case of the latter in combination with the ankle articulation, to a computer for recharging the battery that feeds the electronic devices that are arranged in said artificial limb, updating the firmware, transferring, for a following analysis, the data recorded by the artificial limb to the computer.

Advantageously special software installed on the computer or available in the network analyse the data stored in the memory of the artificial limb and program again the firmware for improving the behaviour of the artificial limb responsive to the wishes of the patient.

Advantageously, in combination or alternatively, with the previous features, on the artificial limb, both in the case of only the knee articulation or in case of a combination of the latter with the ankle articulation, the devices are fed by a rechargeable battery, for example of the type with lithium ions, whose recharging circuit may be connected to the supply circuit out of artificial limb by a primary/secondary connection of a transformer.

This way, the patient can easily recharge the battery while wearing the artificial limb, the aesthetic coating and the clothes.

Advantageously the outer recharging circuit is fed in turn by a battery of larger size, which the patient can wear, for example fastened to the waistbelt, in a backpack, in a pocket etc.

BRIEF DESCRIPTION OF THE DRAWINGS

The invention will be made clearer with the following description of an exemplary embodiment thereof, exemplifying but not limitative, with reference to the attached drawings wherein:

FIGS. 6 and 6A show, in a simplified representation, two hydraulic diagrams, different in the main parts, of a damper operation, according to the invention, adapted to reproduce the functions of the calf muscle;

FIG. 8 shows a cross sectional view of the valve unit integral to the damper with a respective servo-motor (not cross sectioned);

FIG. 9 shows a cross sectional view of the valve unit according to arrows IX-IX of FIG. 8, in the zone where the fluid passes through respective ports;

FIG. 18, shows diagrammatically an above knee prosthesis with hydraulic damper having lamellar piston, with relative graphic diagram in FIGS. 18A and 18B, which ensures a dynamic damping, such that comfort and steadiness are achieved during the gait;

FIG. 23 shows the arrangement of position transducers on the foot in a proprioceptive leg and FIGS. 23A and 23B show their graphic diagram responsive to the relative angles between femur/tibia and tibia/foot;

FIG. 30 shows a diagrammatical view of a motor/reduction gear with freewheel;

FIGS. 31 and 31A show a cross sectional view of an example of a bicycle-type freewheel to which a gear motor is fixed that works as brake/motor mounted on the articulation axis of the knee;

FIG. 36 shows a storage unit in the form of a rechargeable battery applied in a releasable way on the tibial segment.

DESCRIPTION OF THE PREFERRED EXEMPLARY EMBODIMENT

Figure 1:
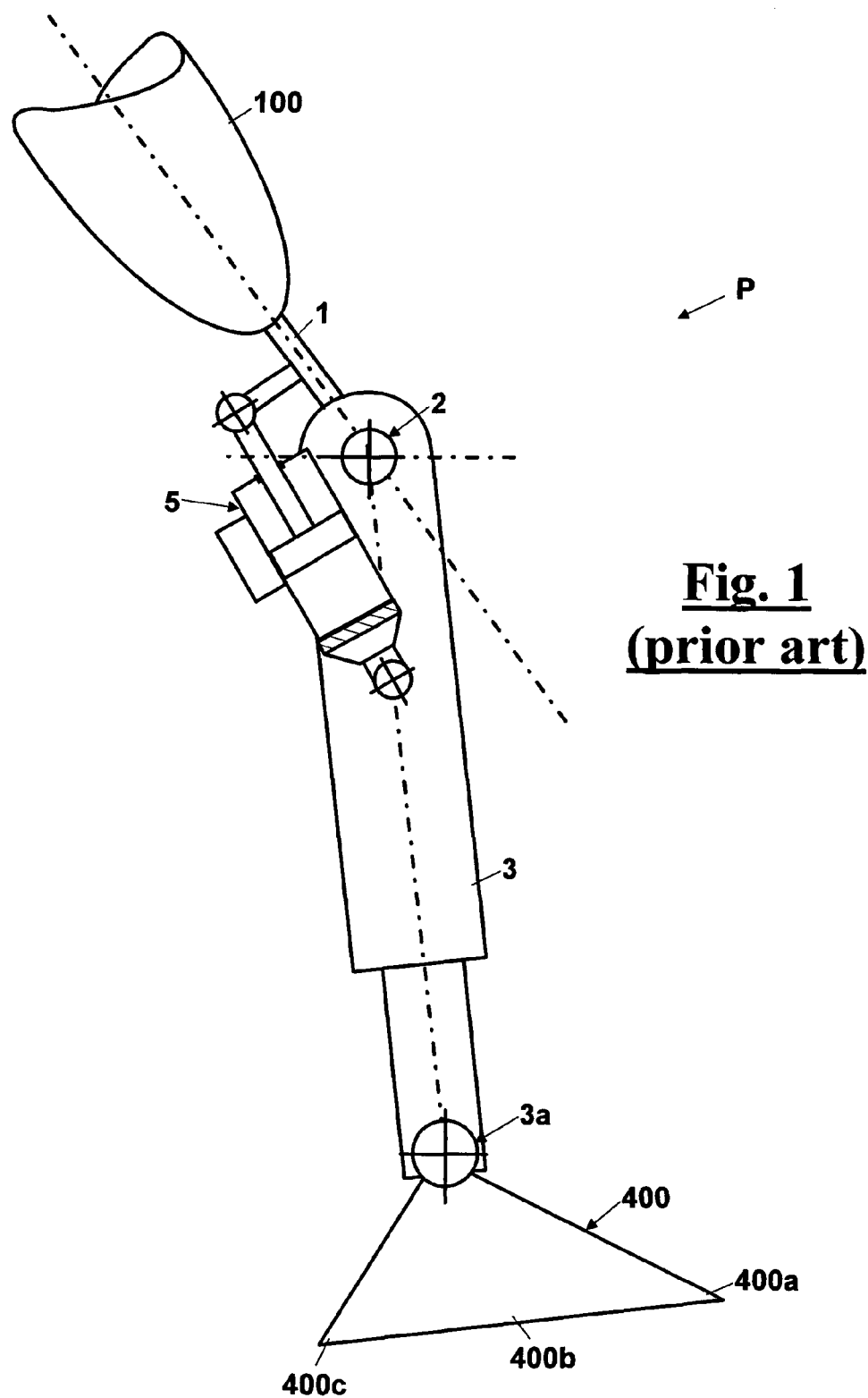
FIG. 1 shows a diagrammatical kinematical view of an above knee prosthesis of prior art.

With reference to FIG. 1, a diagrammatical kinematik view is shown of a prosthesis P of prior art for above-knee amputees, applied to a femoral connection 100 of a possible patient, comprising:
an upper hinge or femoral segment 1 belonging to prosthesis P that accomplishes the connection with the femoral connection 100 of the patient;
an articulation axis 2 that connects femoral segment 1 with a tibial segment 3 and reproduces the movement of a normal knee;
an ankle 3a that connects tibial segment 3 with a prosthetic foot 400;
a damper 5 located between femoral segment 1 and tibial segment 3 that dampens the relative movement between the above described segments and allows the above knee prosthesis P to repeat some of the functions of a normal limb.

In particular, in the above knee prosthesis P, of FIG. 1, femoral segment 1 and tibial segment 3 are pivotally connected to each other about articulation axis 2 that reproduces the knee movements. Furthermore, tibial segment 3 is articulated by the ankle 3a to foot 400 comprising toes 400a, a sole of foot 400b and a heel 400c.

As well known, the knee movements can be divided into a phase so-called swing, between bringing the toes off the ground 400a and landing of heel 400c, and a phase so-called stance, comprising landing of heel 400c, loading the sole of foot 400b and bringing the toes off the ground 400a.

The hydraulic damper 5 connects femoral segment 1 with tibial segment 3 and damps the relative movement of femoral segment 1 with tibial segment 3, so that, especially in the stance phase, but also in the swing phase, tibial segment 3 is braked with respect to connection hinge 2 and to femoral segment 1.

Figure 3:
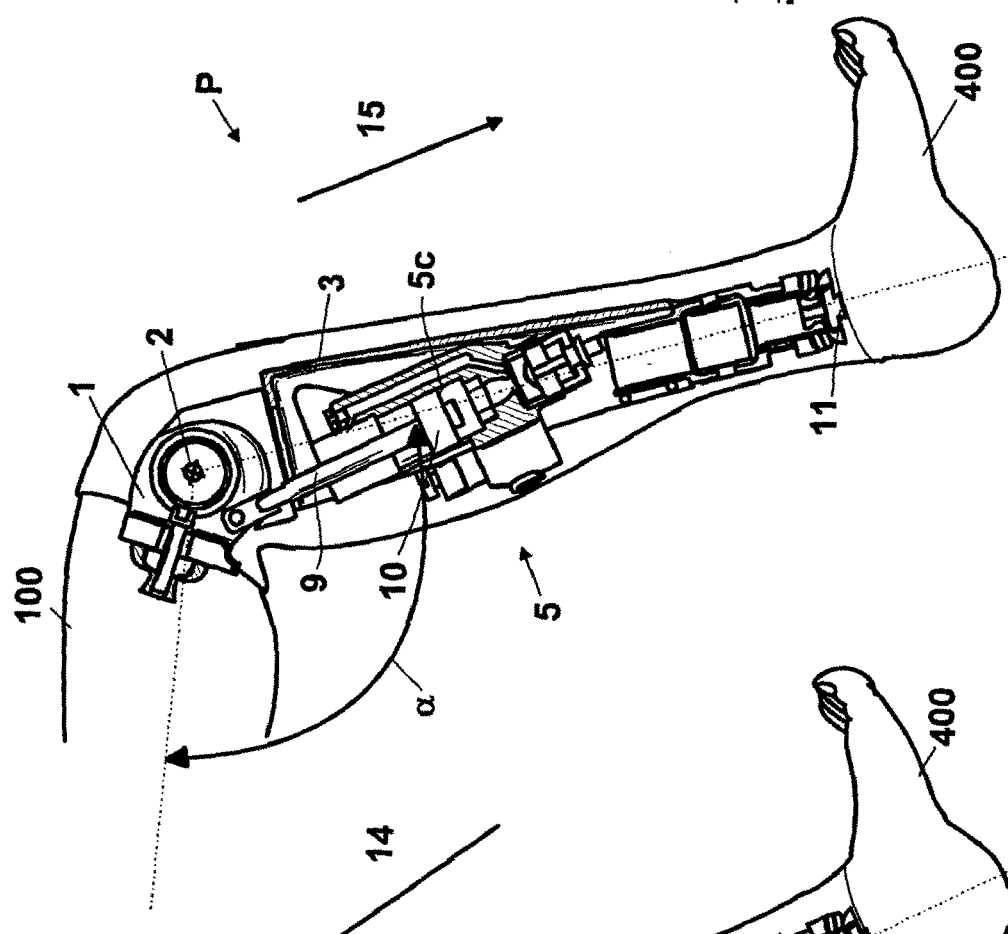
FIGS. 2 and 3 show a cross sectional view of an above knee prosthesis, in a preferred exemplary embodiment, applied to the stump of a patient in two functional gait configurations, without indication of the mechanisms of the ankle.
Figure 2:
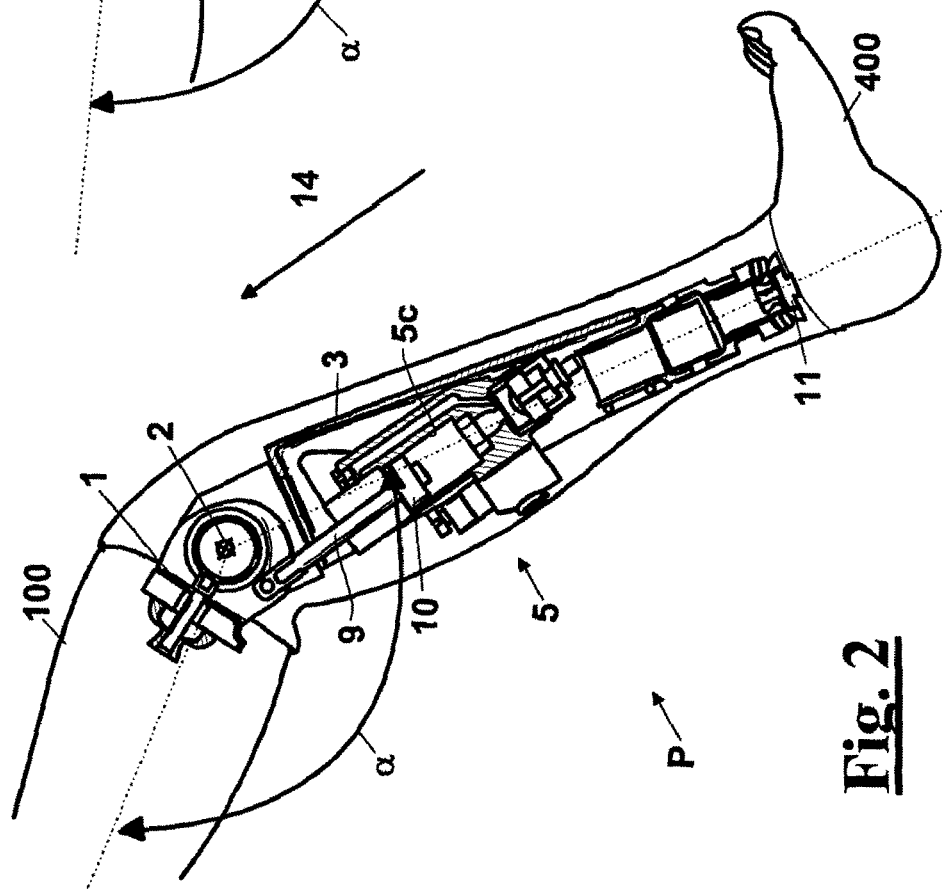

With reference to FIGS. 2 and 3, an above knee prosthesis P is shown, according to the invention, applied to a femoral connection 100 of an amputee; conveniently, in FIGS. 2 and 3, the ankle is not shown in detail and is concealed by an artificial foot cover.

Prosthesis P comprises:
upper hinge or femoral segment 1, which is connected to femoral connection 100 of the patient;
an articulation axis 2, with the function of reproducing the knee movements;
a tibia-calf muscle unit or tibial segment 3 with the function of housing inside the many elements making up prosthesis P such as hydraulic, electric and electronic elements, pivotally connected to femoral segment 1;
damper 5 that reproduces some functions of the calf muscle and ensures to prosthesis P to brake and to allow the sequential swing and stance phases typical of the gait;
a lower hinge 11 for connection with a relative ankle 3a (not shown) and a prosthetic foot 400.

FIGS. 2 and 3 show also damper 5 comprising a cylinder 5c where a piston 10 and a stem 9 connected to each other run and are adapted to carry out a damping reaction responsive to the forces loaded on the prosthesis.

In the present exemplary embodiment damper 5 is a hydraulic damper containing oil in cylinder 5c.

In particular, the alternated motion of piston 10 and of stem 9 in cylinder 5c allow the relative movement between femoral segment 1 and tibial segment 3, allowing to prosthesis P two principal movements, a first extension movement 14, visible in FIG. 2, and a second compression movement 15, visible in FIG. 3. Specifically, tibial segment 3, according to a preferred exemplary embodiment, can rotate about articulation axis 2 of an about 110° angle.

Figure 4:
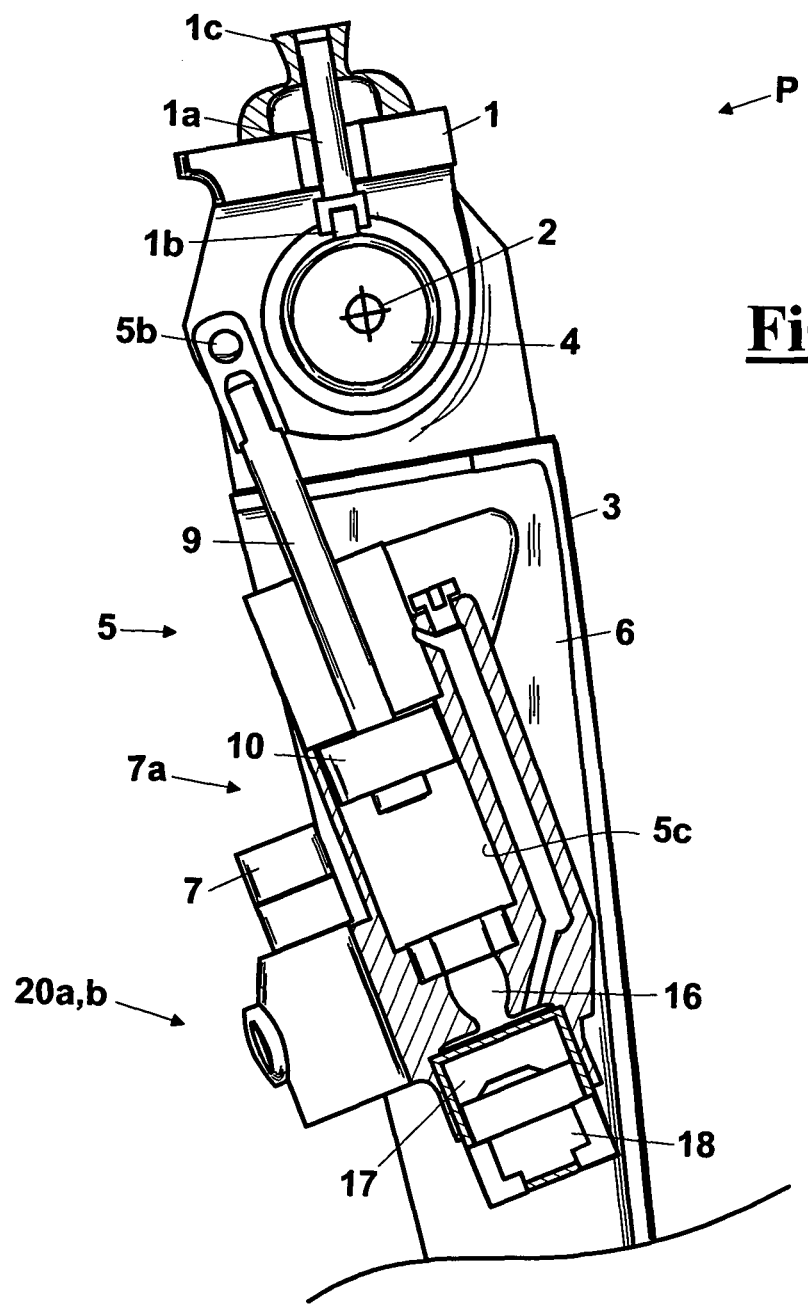
FIG. 4 shows a cross sectional enlarged view of a part of the above knee prosthesis of FIGS. 2 and 3 with piston completely withdrawn, showing in detail the upper hinge, for connecting the prosthesis with the femoral zone of the patient, with the knee articulation and with the damper that controls and limits its movements.
Figure 7:
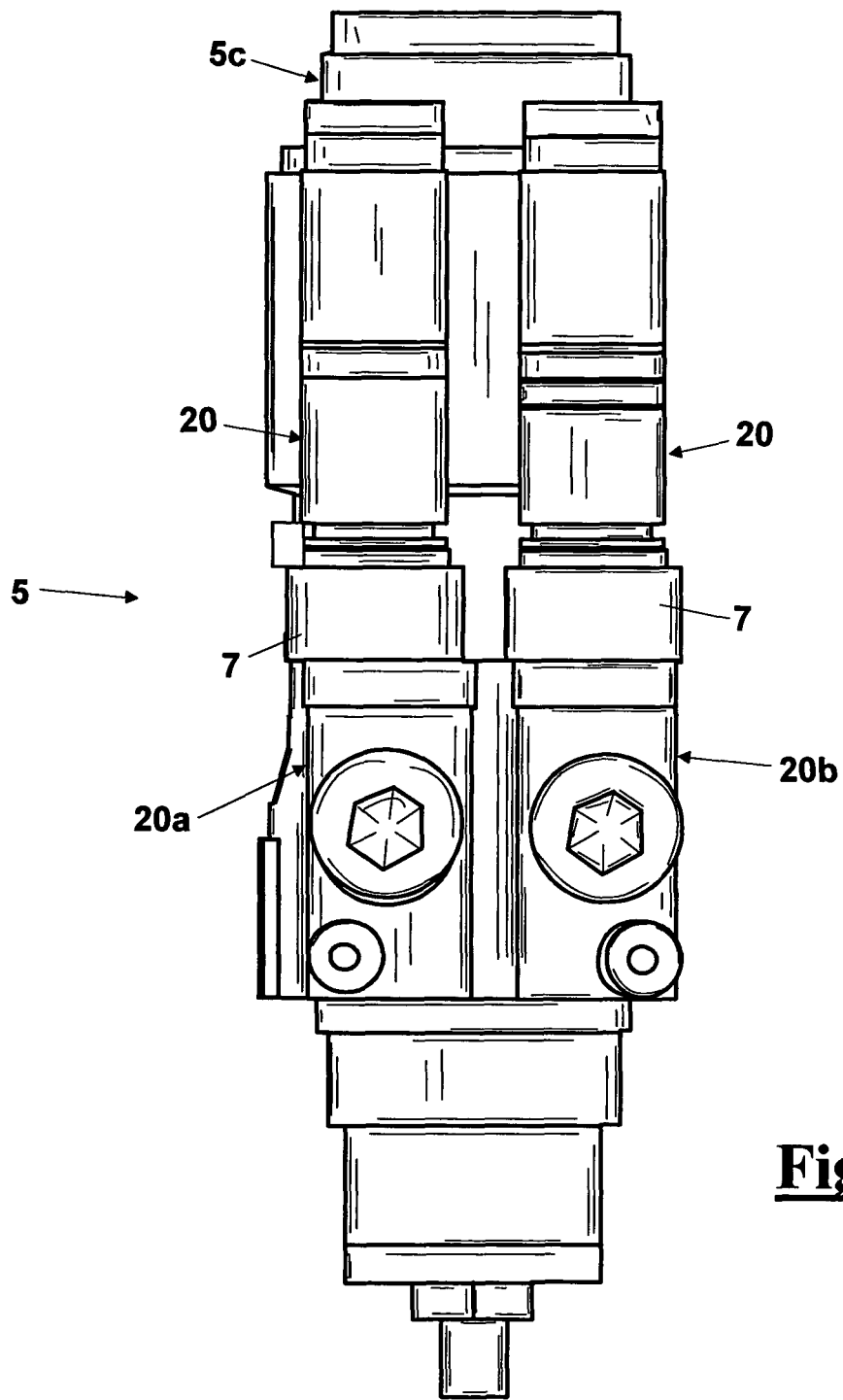
FIG. 7 shows a front view the cylinder of the damper unit, with control unit and servomotors mounted on respective valve groups, which act and operate, separately, the compression and extension phases of the prosthesis.

With reference to FIG. 4, in an enlarged view of the upper part of prosthesis P, in addition to showing again the femoral segment 1, the articulation axis 2, tibial segment 3 that houses damper 5, it shows also a zone 6 housing a battery (not shown—indicated as 80 in FIGS. 32 and 33) for an electric supply of prosthesis P and two valve groups 20a and 20b, integral to damper 5, operated and controlled by relative microprocessors (not shown), as well as servo-motors (not shown and indicated as 20 in FIG. 7). In FIG. 4 an arrow 7a indicates where the servomotors are mounted on the two respective valve groups 20a and 20b. The latter are operated by the microprocessor, not shown, residing in the control unit, which operates the opening and closing movements of the valves (not shown in the figure) that cause the extension movement 14 and the compression movement 15.

In particular, femoral segment 1 comprises a connecting element 1c engaging with femoral connection 100. Connecting element 1c, according to a preferred exemplary embodiment, has prismatic shape.

In FIG. 4 it is also visible, according to an exemplary embodiment of the invention, a gear motor 4, not shown in detail, which is an active element of knee articulation 2, connected to femoral segment 1 by an anti-rotation device (not visible in the figure).

In parallel, the prosthesis comprises a passive element, i.e. damper 5, which is connected to two hinges 5a (shown in FIG. 5) to tibial segment 3 and with a hinge 5b (FIG. 4) to femoral segment 1. In particular, gear motor 4 provides a torque, in some phases of the gait cycle, adapted to adjust the operation of the prosthesis with the needs of the user. For example, the gear motor 4, is operated when, during a slow gait, the inertia of the femur is not enough to align the tibial segment with the femoral segment.

Figure 5:
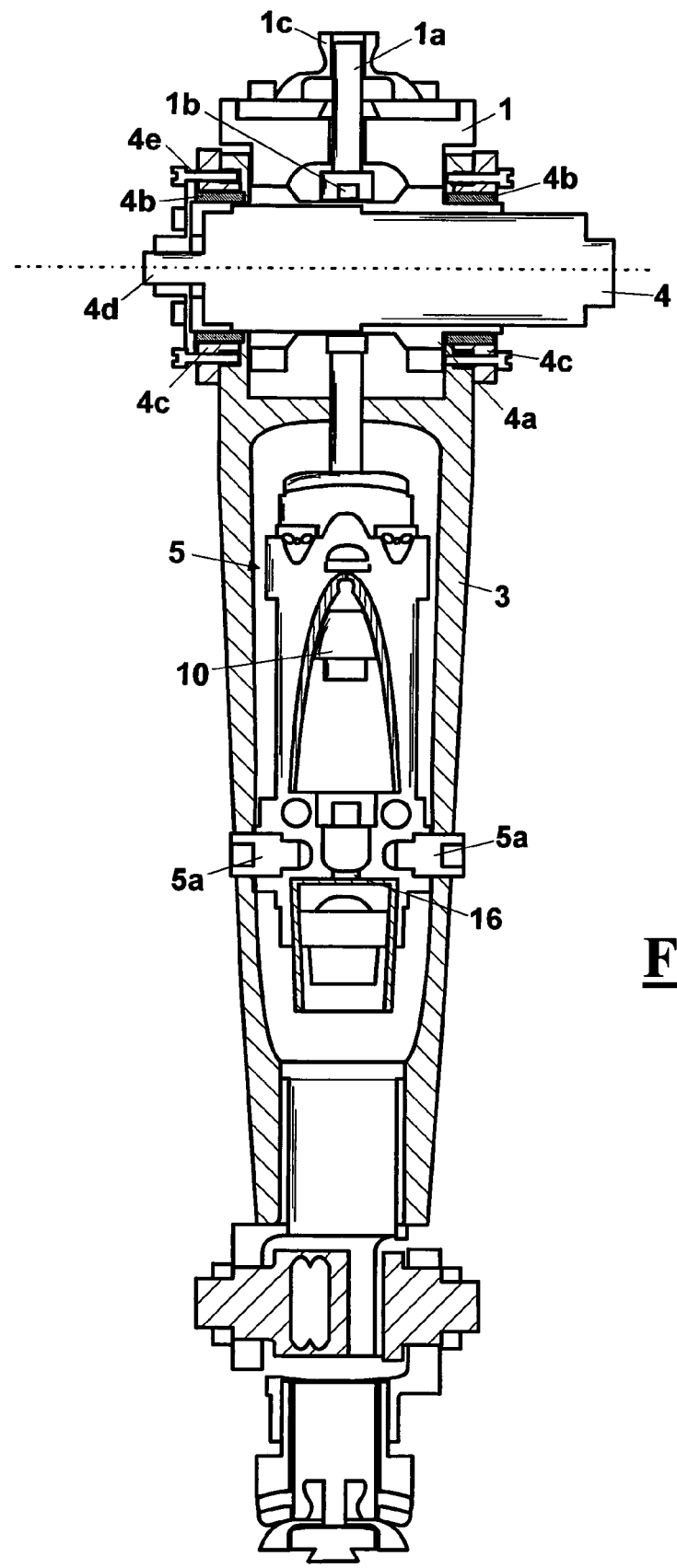
FIG. 5 shows the above knee prosthesis in a cross sectional view, cross sectioned with a axial plane orthogonal to that of FIG. 4, showing also constraint means that connect the damper in the tibia-calf muscle unit.

With reference to FIG. 5, knee prosthesis P is shown according to the invention in a cross sectional view made with an axial plane orthogonal to that of FIG. 4, comprising gear motor 4 mounted in a metal frame 4a, constrained by a connection screw (not visible in the figure) to femoral segment 1. In particular, metal frame 4a rotates on bushings 4b, for example of PTFE, arranged in a support 4c that is constrained by means of screws 4e to tibial segment 3.

Such a connection allows to a shaft 4d of gear motor 4 to be integral to tibial segment 3, while it allows the body of gear motor 4 to be integral to femoral segment 1. In particular, the connection between gear motor 4 and femoral segment 1 is carried out through a shaft 1a and a positive engagement 1b (visible also in FIG. 4). This way, with respect to femoral segment 1, gear motor 4 generates a motion to shaft 4d that causes tibial segment 3 to rotate.

Furthermore, in FIG. 5 the two hinges 5a are shown, which connect pivotally damper 5 to tibial segment 3 and that allow the damper to adjust its angular position responsive to the relative movement between femoral segment 1 and tibial segment 3.

With reference to FIG. 6 a diagrammatical hydraulic simplified view is shown of damper 5, mounted on a prosthesis P, of the types previously described, comprising a cylinder 5c in which piston 10 and stem 9 slide, which are the dynamic parts of damper 5. In particular, stem 9 and the respective piston 10 divide cylinder 5c into two chambers, a chamber A and a chamber B, containing hydraulic oil.

During the extension 14 or the compression 15 of prosthesis P, the oil flows from chamber A to chamber B. In particular, since the volume of stem 9 that enter/exits from cylinder 5c has to be compensated in volume, an external compensation chamber is provided 16 partially filled with oil 13 and with air 18 in pressure.

In a different exemplary embodiment, not shown, alternatively to air 18 a spring can be provided with a determined elastic constant.

The diagrammatical hydraulic view of damper 5, of FIG. 6, comprises furthermore:
  a channel E_1 extending from chamber B to compensation chamber 16, between which a check valve VN_1 without pre-charge and an adjustment valve remote 19_E are arranged;
  a channel E_2 extending from compensation chamber 16 to chamber A, between which a check valve VN_2 without pre-load is arranged;
  a channel C_1 extending from chamber A to compensation chamber 16, between which a check valve VN_3 without pre-charge and an adjustment valve remote 19_C are arranged;
  a channel C_2 extending from compensation chamber 16 to chamber B, between which a check valve VN_4 is arranged;
  a channel 14' that connects a chamber 9b of an oil sealing chamber 9a to chamber 16 and is used to avoid pressure peaks in the oil sealing chamber 9a as well as it can be used as compensation chamber and air emptying chamber in a phase of filling damper 5.

In addition, two further channels can be considered on the piston, in particular, a channel 10A and a channel 10B that act as check valves with pre-loaded spring and with intrinsic damping characteristics. In particular, these channels bring directly into contact chamber A with chamber B and act as possible safety systems for pressure peaks.

The operation of damper 5 provides mainly a compression 15 and an extension 14. In particular, the compression phase 15, during the operation of damper 5, comprises:
  the movement of piston 10 and of stem 9 so that the volume of chamber A decreases while the volume of the respective chamber B increases. This way, the depression created in channel E_1 and in channel E_2 causes check valves VN_1 and VN_2 to close. The oil flows then through channel C_1 pushed by the compression of piston 10, and opens valve VN_3. Then the oil at the outlet of valve VN_3 finds the resistance of valve 19_C adjusted with a suitable inlet pressure. The oil, once passed the resistance of valve 19_C, enters then compensation chamber 16. In particular, the amount of oil, which is caused by stem 9 at the inlet, remains in compensation chamber 16 while the amount of oil attracted by upper chamber B enters through channel C_2 and opens valve VN_4.

The extension phase 14 comprises instead:
  The movement of piston 10 and of stem 9 so that the volume of chamber A increases while the volume of respective chamber B decreases. This way, channel C_1 and C_2 are closed by check valves VN_3 and VN_4. The oil flows then through channel E_1, thus opening valve VN_1 and meeting the resistance of valve 19_E, which is adjusted also according to a given output pressure. The oil enters compensation chamber 16 and the exiting amount flows from chamber 16 to chamber A through check valve VN_2. Channel 14' is used in the presence of pressure peaks during the extension phase acting as low pressure system on the sealing member.

Then, for the extension phase the braking action is of "pure leakage" type with leakage area that is variable responsive to position, with braking action that is activated in the last 7°-10° of the knee flexion stroke. The compression of the limb is carried out, instead, substantially with a plurality of inverse phases.

In the alternative exemplary embodiment of FIG. 6A, instead, there is an adjustment of the braking action during the extension phase of "geometric" type. More precisely, during the extension phase, instead of channel 10A, a leakage stem 9' is provided, where holes 9'' are made with different size from one another and that allow a progressive passage of oil. In this case, in fact, during the extension phase oil returning channel C_2 is closed by check valve VN_4 and does not allow the oil passage. This way, the oil flows from chamber B to chamber A through the channel present on stem 9', owing to check valve VN_5 arranged on such channel. In particular, the oil flows from transversal holes 9'' on stem 9' into the channel made in stem 9' and opens valve VN_5. Conversely, during the compression phase the check valve on the stem is blocked.

Also it is to be noted that the oil flow is adjusted by transversal holes 9'' on stem 9'. When they are in the sliding bush of stem 9', they not take part to the oil flow, and is reduced therefore the cross section of the oil passage, such that the braking action tends in this way to become stronger, in a way as above defined "geometric".

FIG. 7 shows a view of cylinder 5c of damper 5 having outside the two valve groups 20a and 20b connected to the respective servo-motors 20. In particular, the servomotors 20 transmit a torque, adjusted by the respective microprocessor control unit (not shown) for each valve unit 20a to 20b, which operates and adjusts the opening and the closing steps of a respective inner valve 24 (visible in FIG. 8).

In particular, the damping action of damper 5 is obtained by adjusting at the same time or separately the extension phase 14 and the compression phase 15 of FIGS. 2 and 3 according to the needs deriving from particular gait conditions. Each servo-motor 20 is mounted separately on the respective valve unit 20a or 20b, for controlling separately both the extension phase 14 and the compression phase 15.

FIG. 8 shows furthermore, in an enlarged view, one of the two servo-motors 20, depicting the mechanical and hydraulic connection with the relative valve unit 20a (or 20b not shown). In particular, the valve unit 20a, depicted in cross section comprises:
the microprocessor control unit, not shown, which operates and adjusts a valve 24, where valve 24 has a fixed body 24a on which apertures 19 are made, and a tap 24b that, by rotating, opens and blocks apertures 19 (see also FIG. 9);
a sleeve joint 23 for transmitting the torque between a shaft 21 of servo-motor 20 and tap 24b. In particular, tap 24b transmits its rotational movement to valve body 24, in order to adjust the opening and the closing movements of apertures 19;
a bearing 22a where sleeve 23 turns, and a mounting ring element 23a adapted to support it;
a seal element 23b for the oil flowing in valve body 24 and an end stop 25 for valve 24a.

In particular, the microprocessor unit is connected by cables (not shown) to a Hall effect angular transducer 7 and to servo-motor 20.

FIG. 9 shows in particular, a view of the cross section according to lines IX-IX of valve 24a, tap 24b and valve body 24. In particular, apertures 19 are shown, which allow the oil to flow, and are arranged in succession and have an variable size. This way, valve 24a in the relative rotation about valve body 24, where apertures 19 are made, adjusts the partial or total opening of the above described apertures 19 allowing the oil to flow, according to the damping intensity required by the prosthesis.

Figure 10:
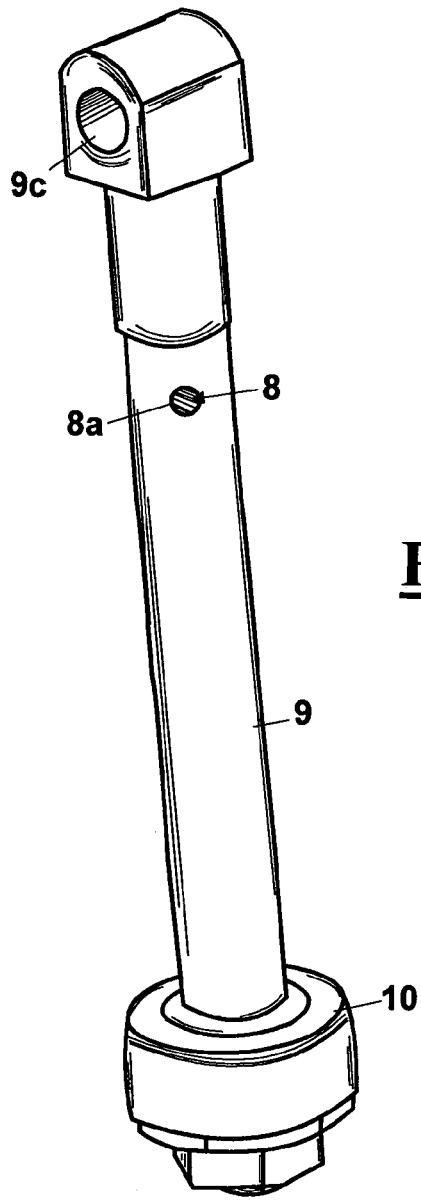
FIG. 10 shows a perspective view of a possible exemplary embodiment of a stem-piston device, showing a ring-like force transducer mounted in the stem.

With reference to FIG. 10, a perspective view shows stem 9 and respective piston 10 that is the active portion of damper 5 and divides cylinder 5c into two chambers A and B (shown in FIG. 6). In particular, on stem 9 a hole can be made 8a, with an axis perpendicular to the axis of stem 9, where a dynamometer 8 is inserted, so-called "Morehouse ring". Obviously, on the stem other types can be applied of force transducers.

At the upper end of stem 9, furthermore, a housing 9c is made for connection with its antithetic part (not visible in the figure) that represents the hinge 5b of femoral segment 1 (visible in FIG. 4).

Alternatively, or in addition, in a way not shown, as provided by the present invention, force transducers can be provided on the damper at other points, such as at housing 9c of upper hinge 5b (see FIG. 10), or in the housing lower hinge 5a, for example using strain gauges or load cells, or ring transducers.

Figure 11:
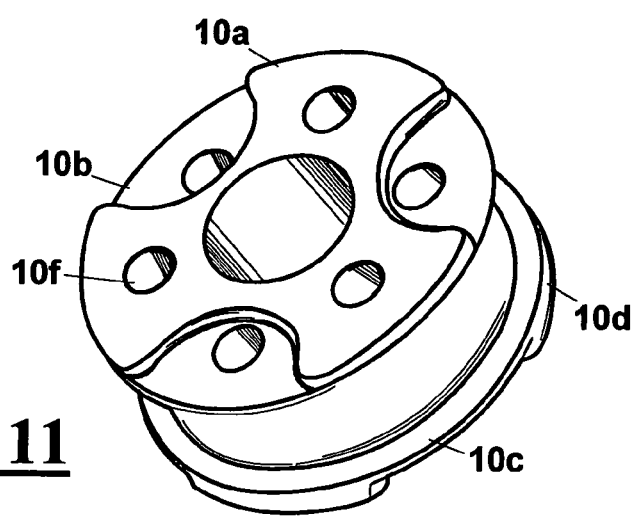
FIG. 11 shows a perspective view of the piston member of FIG. 10 separated from the stem.

FIG. 11 shows a perspective view and detailed of piston 10, of FIG. 10, which is part of damper 5. In particular, piston 10 comprises "faces" 10a, 10b, 10c and 10d and is arranged for being covered by metal blades and discs of different thicknesses and diameters (shown in FIG. 12) that act as springs and open the apertures according to the speed of the stem in cylinder 5c.

Figure 12:
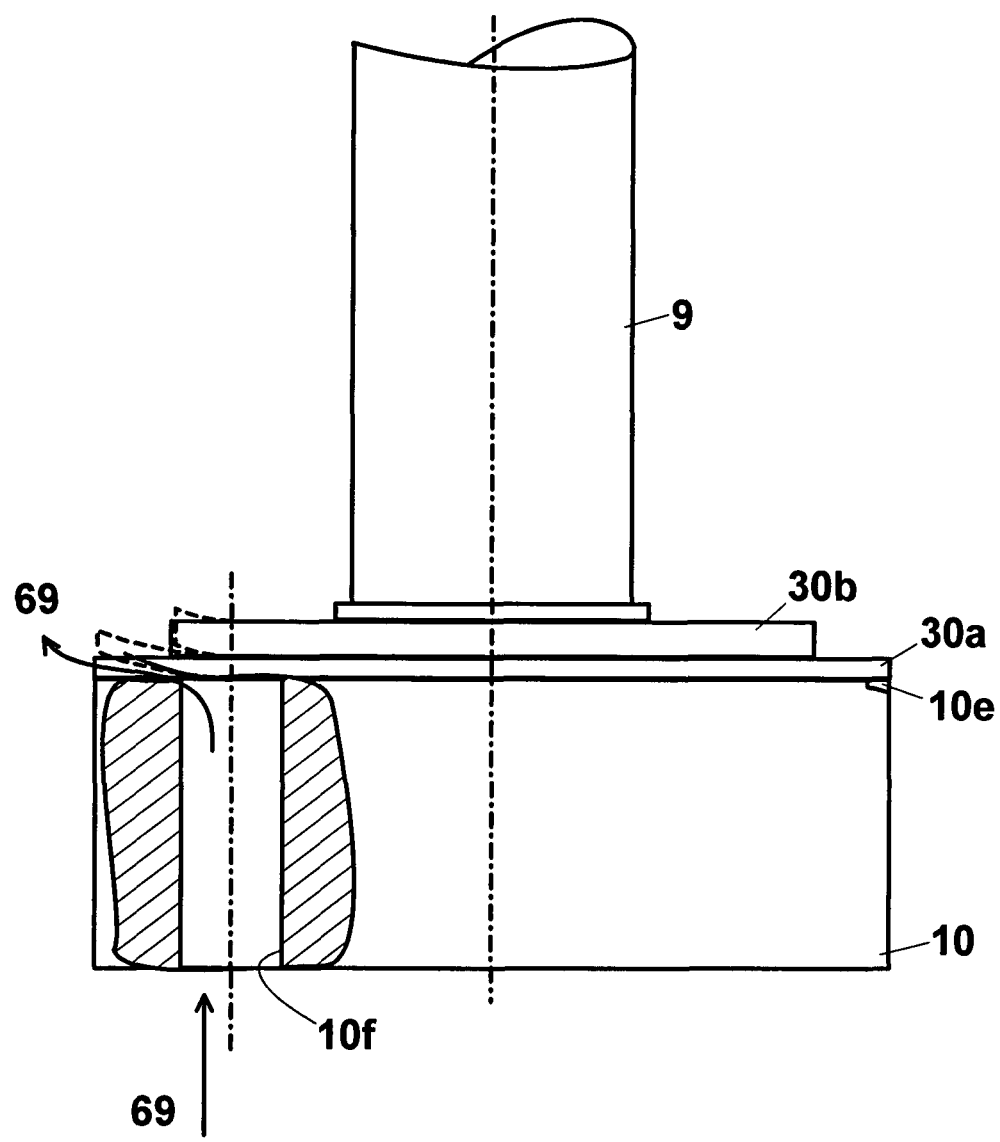
FIG. 12, shows a particular "four faces" stem-piston similar to that of FIG. 11, in a step of its operation, in particular, when the oil outflow occurs, passing through the channels made inside, from one surface to the other.

FIG. 12 shows in an enlarged view piston 10 and the relative stem 9 comprising, according to a preferred exemplary embodiment, a first lamina 30a and a second lamina 30b with diameter and thickness less than first lamina 30a. In particular, first lamina 30a is located at the face 10a of piston 10 (visible in FIG. 11) whereas second lamina 30b is located at first lamina 30a. Specifically, blades 30a and 30b are located at piston 10, such that the respective axes of symmetry coincide with the axis of stem 9.

In detail, first lamina 30a creates a gap 10e between face 10b of the piston (visible in FIG. 11) and the lower surface of lamina 30a same. In particular, gap 10e allows a minimum oil flow from chamber A to chamber B. More precisely, the movement of piston 10, shown in FIG. 12, represents the compression phase 15 in cylinder 5c. In the compression movement 15 the oil flows from chamber A to chamber B through a channel 10f. The force of the oil flow 69 passing through channel 10f causes a deformation of the blades 30a and 30b, allowing the leakage of oil from one chamber to the other. Specifically, blades 30a and 30b control a higher or lower oil flow responsive to the force exerted on the damper and to the speed of piston 10. Under similar operative steps as described above, also the extension phase 14 of the prosthesis (not shown in the figure) can be controlled.

Figure 13:
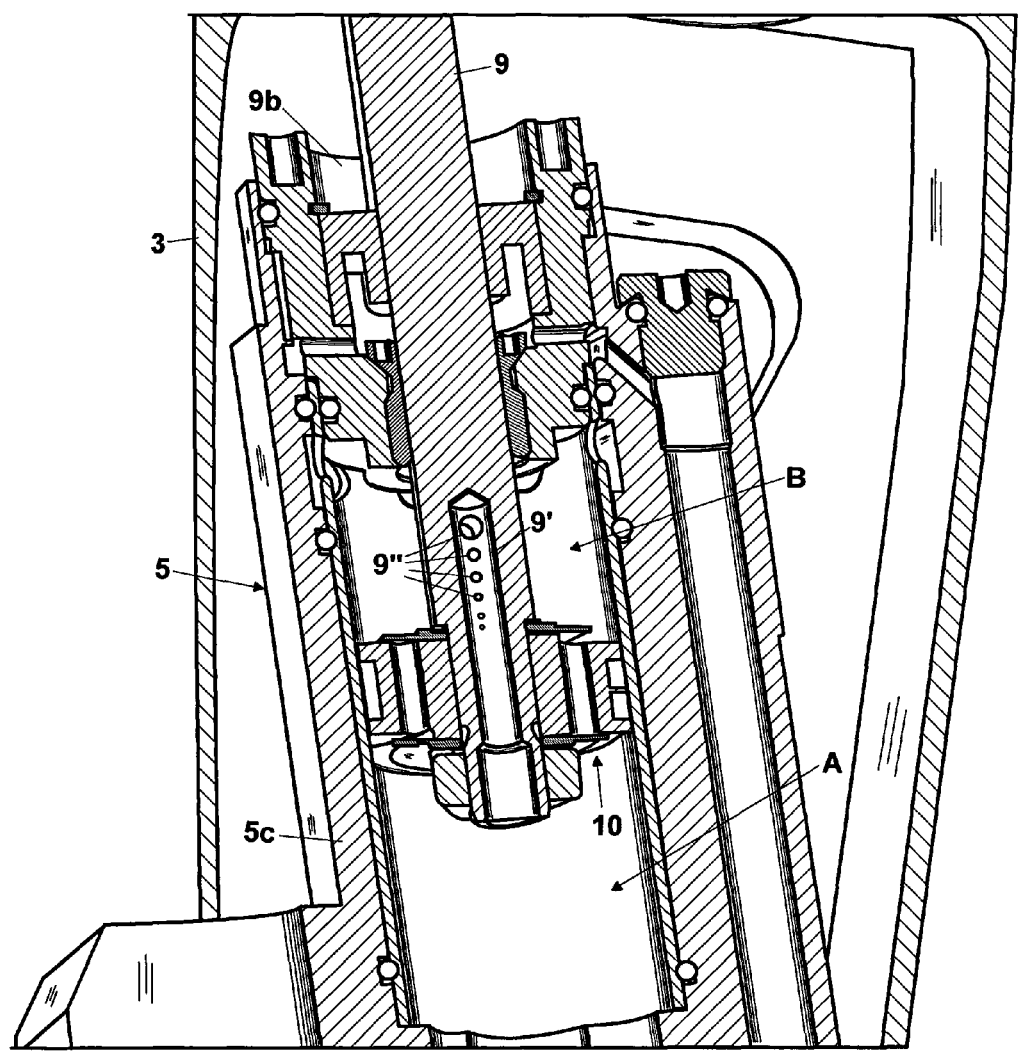
FIG. 13 shows a cross sectional view of the geometrically adjustable braking device.
Figure 14:
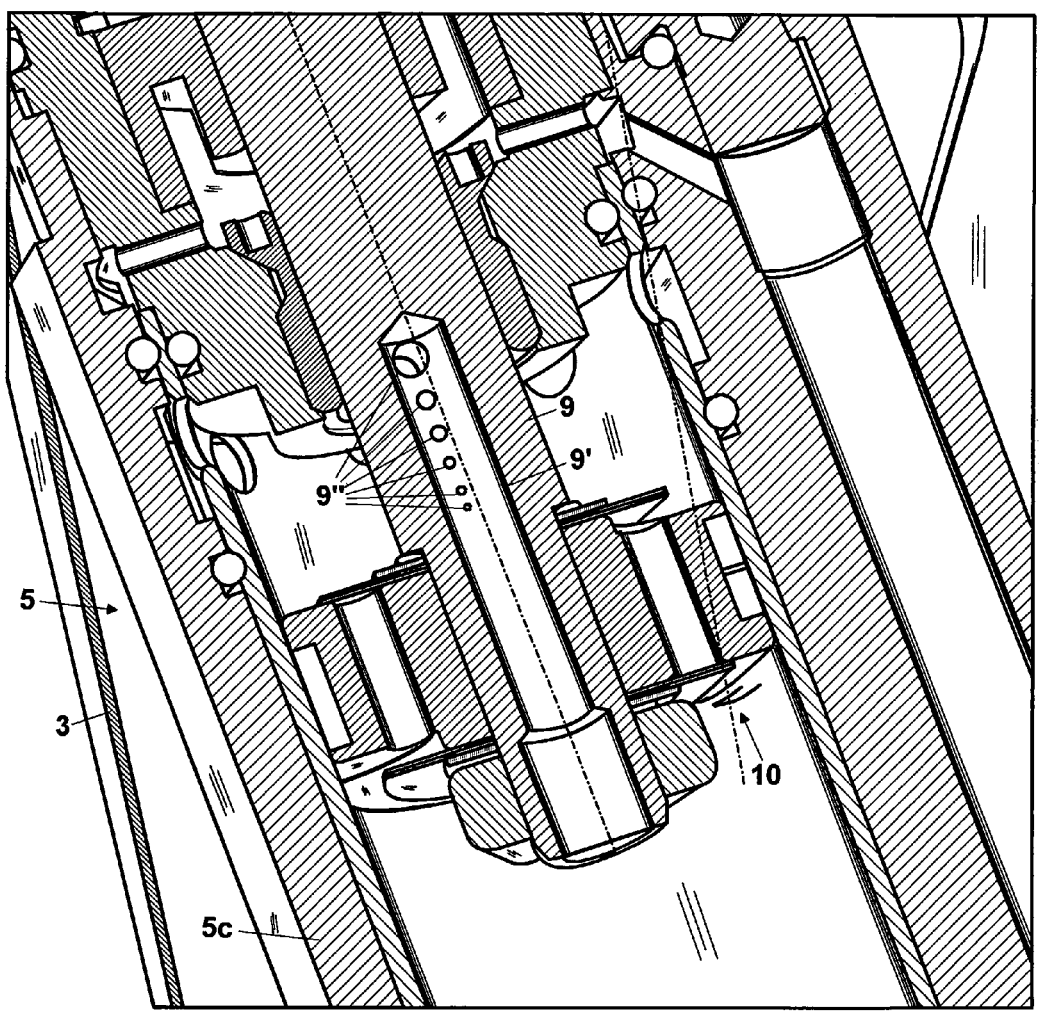
FIG. 14 shows an enlarged view of the device of FIG. 13.

FIGS. 13 and 14 show a cross sectional view of the device that carries out the braking action of the knee prosthetic P with a geometric control, as diagrammatically shown in the hydraulic circuit of FIG. 6A. In particular, in this device the oil flow is adjusted by transversal holes 9'' made on stem 9'. This way, when these are within a sliding bush of stem 9', the oil flow stops, so that the cross section of the oil passage stops and therefore the braking action increases.

In an exemplary embodiment of the present invention, with reference to FIG. 1, 5 and showing again a diagrammatical view of the prosthesis for above-knee amputees P, also in addition to any of the exemplary embodiments above described, the following are provided:

- a transducers unit 31 for receiving the data on the surroundings and, in particular, to allow acquisitions of information on relative position with respect to the femur, or also on force;
- a microprocessor 32 for computing data and defining the best logic of control and choice of the operations to carry out to ensure comfort and a safe gait.
- an accumulator 33 of energy that acts in a way suitable to ensure storing energy of first species (noble) obtained by recovering energy during the gait and using it in the steps of demand of energy from the device;
- a constraint having an adjustable stiffness, comprising a device capable of providing/dissipating/recovering energy during the gait provided at the knee joint, indicated as 34, or at the ankle joint, indicated as 35, or both.

Figure 15:
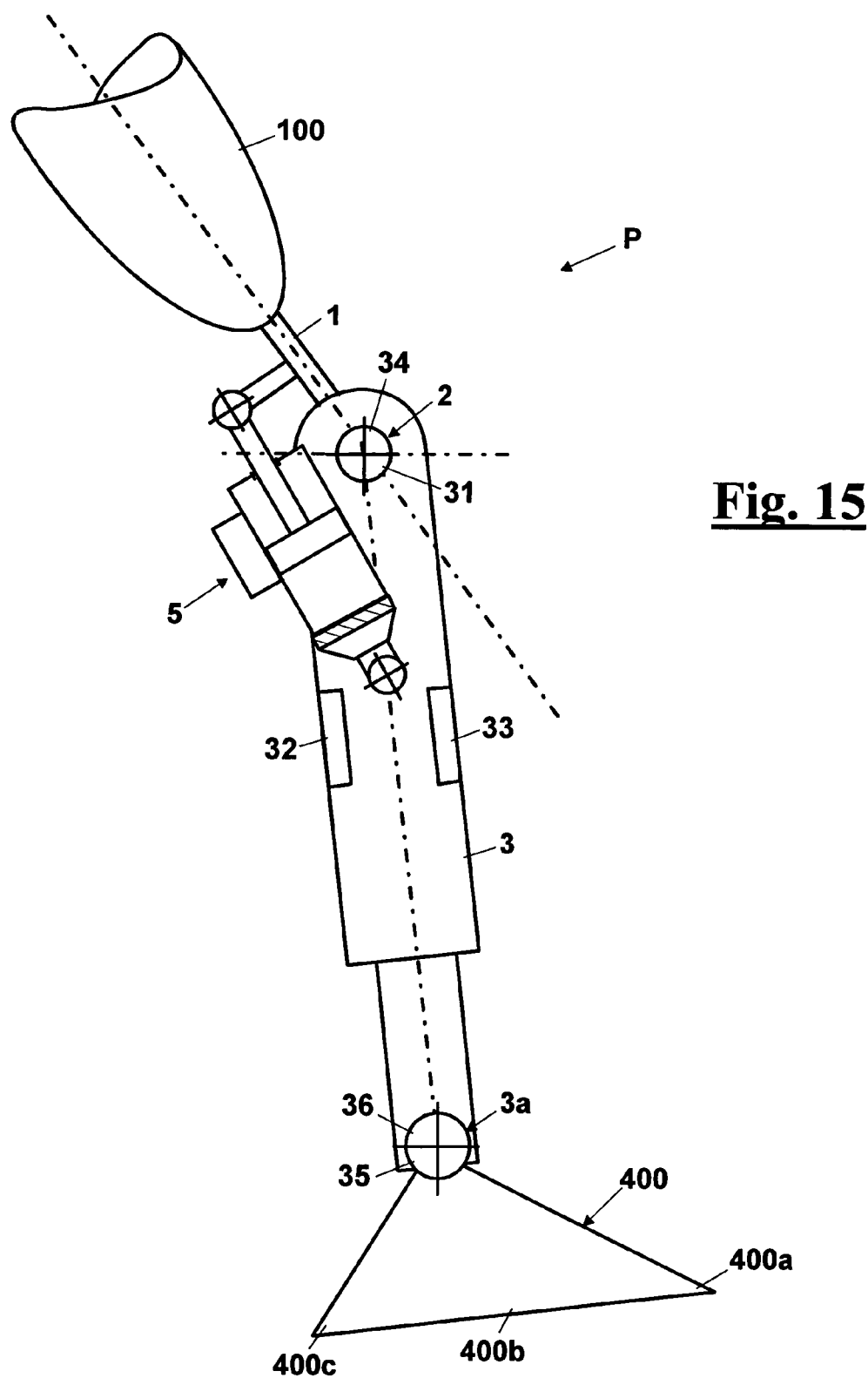
FIG. 15 shows a diagrammatical kinematical view of FIG. 1 illustrating the position of transducers adapted to receive and analysing data on the surroundings.
Figure 16:
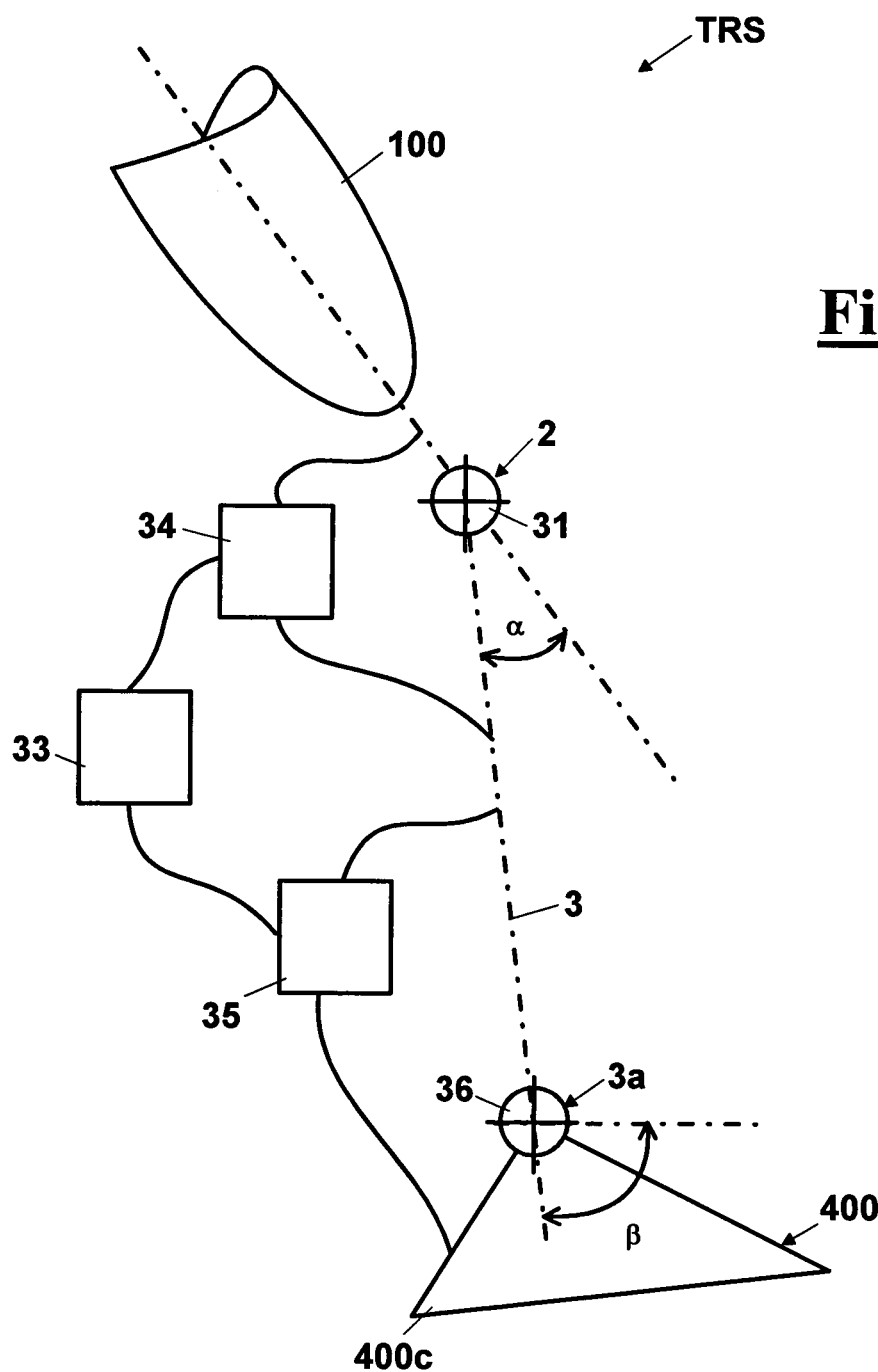
FIG. 16 shows a diagrammatical kinematical view of the above knee prosthesis, composed by energy recovery elements between femur/tibia and tibia/foot as well as by devices for receiving data on the surroundings.

In FIG. 16, what shown in FIG. 15 is depicted as block diagram, i.e. a knee-ankle TRS (Total Recovery System) comprising:

- a recovery device 34 between femoral segment 100 and tibial segment 3;
- a recovery device 35 between tibial segment 3 and foot 400;
- an accumulator 33 of energy;
- a data acquisition transducer 36 for ankle 3a;
- a data acquisition transducer 31 in the articulation axis 2.

In particular, the operation of the TRS allows the articulation axis 2 and the ankle 3a to interface with each other exchanging data and energy.

As well known, during walking on a plane ground during a large part of the gait the articulation axis 2 works dissipating the energy supplied, since the energy supplied by the femur 100 (relative motion between femur and tibia) lifts and launches tibia 3. The articulation axis 2 operates reducing the swinging action of tibia 3 and supplying safety with a stabilizing moment during a support phase. During these phases, the dissipated energy, normally at the articulation axis 2, can be recovered using a suitable storing device in a unit that has a function of energy accumulator 33. The energy can be exploited partially from the same articulation axis 2, for example supplying energy in some phases of the gait cycle and, in particular, when accelerating tibia 3, to ensure a realignment with femoral segment 1, and partially by the ankle 3a or for other objects.

During the gait, the ankle 3a works both as dissipative element and as active element. In particular, in the first phase of the gait starting from landing the heel 400c, the ankle 3a acts as system of a spring and a damper in parallel, where an energy dissipation occurs in the relative movement of foot 400 with respect to tibia 3. Then, when heel 400c is not compressed any more, foot 400 acts as active element supplying energy for lifting the limb. During the dissipative phase, the energy surplus can be accumulated in the accumulator 33 at the articulation axis 2. In analogy to what occurs at articulation axis 2, ankle 3a uses energy from the accumulator 33 during its active phase, using another active element in parallel to the spring provided in the ankle.

The energy storage unit 33 can be for example arranged on the tibia, as indicated in FIG. 15. Alternatively, the storage unit is integrated in the motor 34 mounted on the hinge of the knee.

The device 34 integrated with the device 33, allows to act on the behaviour of the ankle 3a and of the articulation axis 2, such that the behaviour of the integrated device 34 and 33 is suitably phased; the position data of the articulation axis 2 and of the ankle 3a are continuously monitored by a transducer 36 and by a transducer 31, which administer also the exchange of data of the forces of the two transducers.

Figure 17A:
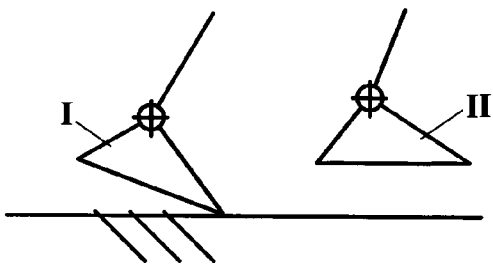
FIGS. 17, 17A and 17B show the so called Toe Clearance respectively in case of risk for the toes to hit the ground during the swing phase (I) and absence of interference of the toes with the ground during the swing phase (II) with relative diagram.
Figure 17B:
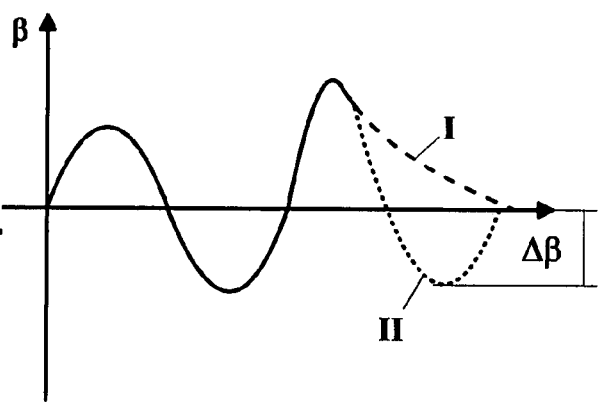
Figure 17:
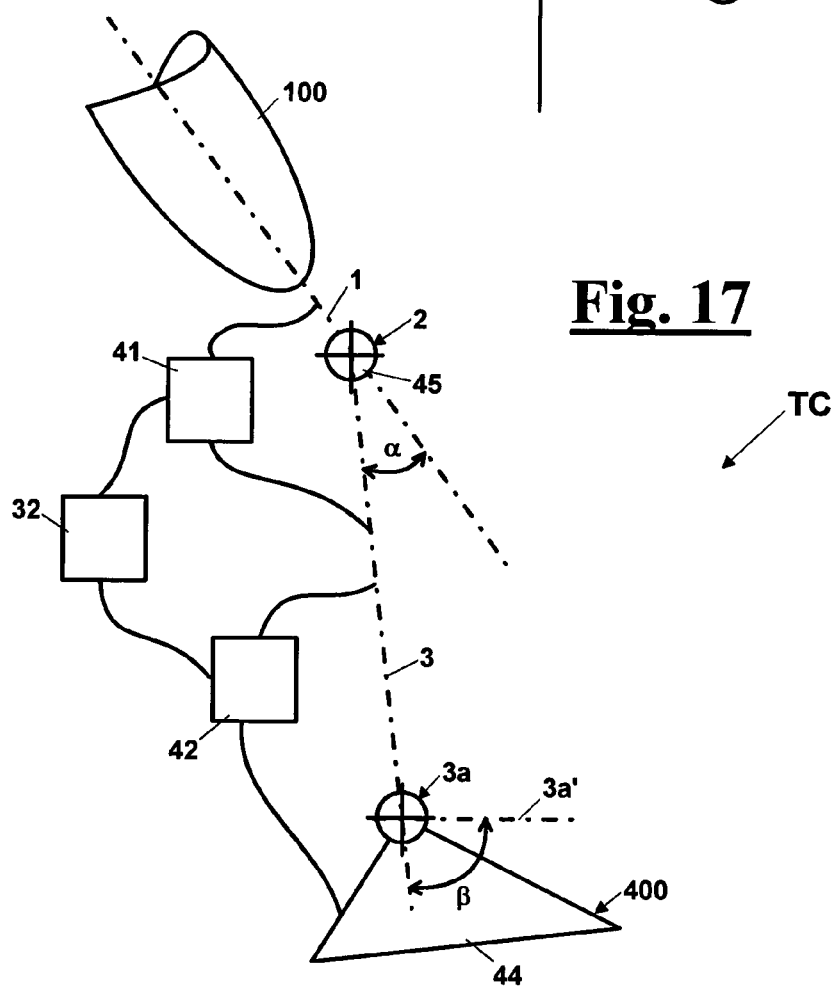

FIG. 17 shows how the motor/generator on the knee and on the ankle can form a knee-ankle system TC (Toe Clarence) comprising:

- a device 41 to adjust and control the articulation axis 2 integrated in the motor/generator 34 of FIG. 16;
- a device 42 to adjust and control of the ankle 3a integrated in the motor/generator 35 of FIG. 16;
- The microprocessor 32 that works as unit decisional;
- two transducers 44 and 45 of interface ground/leg for defining the status of the gait.

Furthermore, an angle α is defined determined between femoral segment 1 and tibia 3 and an angle β determined between tibia 3 and an axis 3a' orthogonal to tibia 3.

In particular, at a low speed it is normal that the minimum dynamic effect of the femur 100 determines a small lifting of prosthetic foot 400, that, owing to the stiffness of foot 400, ends for not exceeding the TDC between femoral segment 1 and tibia 3 in phase of swing, but can generate a risk for the toes to hit the ground I during the swing phase (FIG. 17A).

During the gait on a plane ground in elder patients or in patients in phase of recovery after amputation, it is easy that realigning tibia 3 with femoral segment 1 is problematic. In a first case, a Toe Clearance situation occurs, i.e. of lack of clearance between toes 400a and ground during the gait (FIG. 17A I). In this phase, the minimum dynamic effect provided by the femur 100 causes a not appropriate lifting action on tibia 3 that has a relative angle with respect to femoral segment 1 very low with the risk for the toes of foot 400 to hit the ground. In a latter case, once passed the TDC between femoral segment 1 and tibia 3, the problem arises of an effective realignment in case of minimum swinging action of tibia 3. In order to solve the first problem, i.e. toe clearance during the swing phase, the knee-ankle system TC identifies the current configuration according to the data determined by the transducers and compares these data with the values of the corresponding ideal configuration. This way, changing the angle β of incidence of foot 400 with respect to tibia 3, the risk for the toes can be avoided to hit the ground during the swing phase (visible in FIG. 17A II). Similarly, supplying energy to the articulation axis 2, a realignment is ensured of femoral segment 1 and of tibia 3 for low gait speed.

The knee-ankle system TC is therefore characterised by the presence of devices that control the bidirectional flows of energy towards and from the joints of the system, allowing, thus, by means of suitable control logics, to determine conditions of the gait optimized with respect to safety, comfort and energy saving.

FIG. 18 shows diagrammatically an exemplary embodiment similar to that shown in figures from 4 to 14, i.e. an above knee prosthesis P on which a hydraulic damper 46 is mounted comprising two interfacing chambers 46b, 46c, by a hydraulic cylinder 46a with two valves in parallel: a leakage valve 46e and a lamina valve 46d, characterized by the possibility to exploit a piston with 2 or 4 faces (visible in FIG. 11). The combination of the two valves 46e and 46d is like an equivalent valve with variable area responsive to the speed of the piston 46a. This solution determines a progressive braking behaviour with equivalent control in force instead of position. The result is a very progressive dynamic behaviour that excludes sudden differential reactions of the damper in case of impulsive loads; such reactions are typical of the traditional pure leakage systems that have fixed area apertures. Therefore the damper is like low-pass filter, capable of filtering and not transmitting to the patient the impulsive loads and assuring therefore a higher comfort in the gait. It should be noted that the above knee prosthesis P can be controlled acting on the stiffness of the lamina valve 46d or on the relative area of the by-pass, thus ensuring translation of the braking curves IV, V, VI, VII of FIG. 18B, obtaining high equivalent stiffness for the phases of support and adjustable for other dynamic phases of the gait, by damping and stopping the phase of realignment or of lifting the heel at high gait speeds.

Figure 19A:
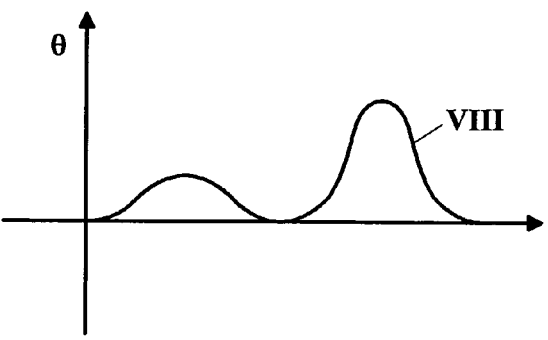
FIGS. 19A and 19B show, furthermore, the graphic diagram of the knee and of the ankle.
Figure 19B:
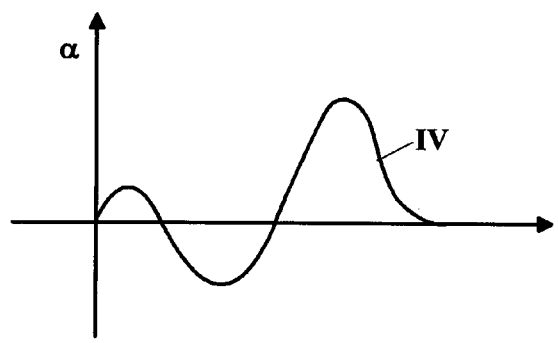
Figure 19:
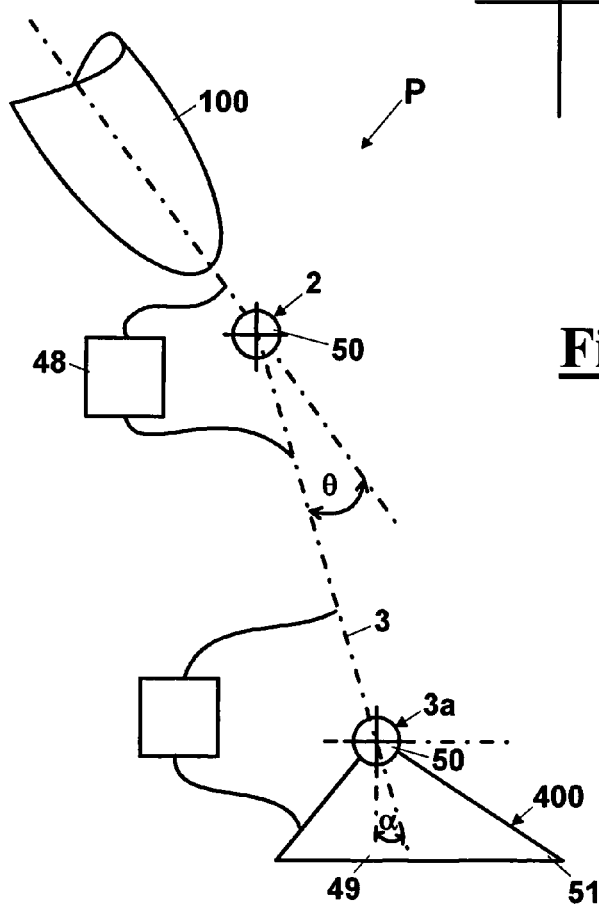
FIG. 19 shows diagrammatically an arrangement of the interface and control transducers with respect to the surroundings with the devices that make up the prosthesis same.

FIG. 19 represents diagrammatically a possible embodiment of the invention on an above knee prosthesis P, comprising transducers 48 that allow detecting data on the inner deformation of prosthesis P, a transducer 49 on the prosthetic foot sole 400, position transducers 50 and a position transducer for acquisition of data 51 on the surroundings. In particular, such a prosthesis allows an above-knee amputee to perform a natural gait, developing a system for adjusting and controlling the gait that reproduces partially the proprioceptive functions, owing to activity of receptors similar to those of the muscles and of the tendons, as well as the view and the spatial relative position. Prosthesis P, if controlled in this way, may have aspects of predictivity with respect to the surroundings, in a way suitable to ensure the use of control logics that is suitable in the actual gait, where the limb seeks safe and comfortable responses.

Figure 20:
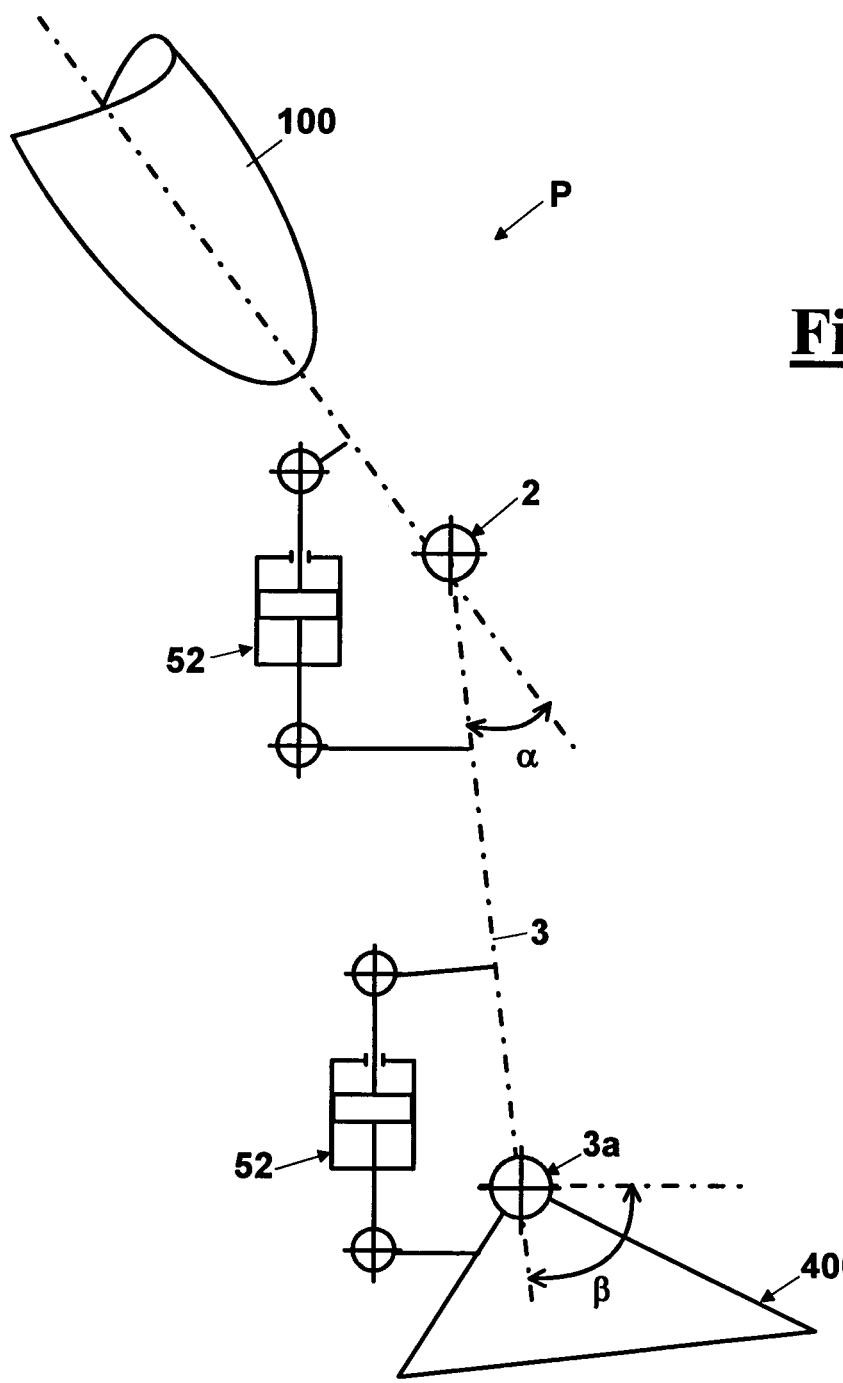
FIG. 20 shows diagrammatically an above knee prosthesis that provides magnetic motors applied as alternative to hydraulic dampers.

With reference to FIG. 20, a possible embodiment of the invention is shown diagrammatically on an above knee prosthesis P, comprising low noise motors/generators. In particular, according to a preferred exemplary embodiment, such motors/generators 52 are ultrasonic pulse motors or linear magnetic motors, like those used in some automotive applications. Furthermore, the device is characterized for giving to motors 52 a function of generator and of electronic damper.

Figure 21:
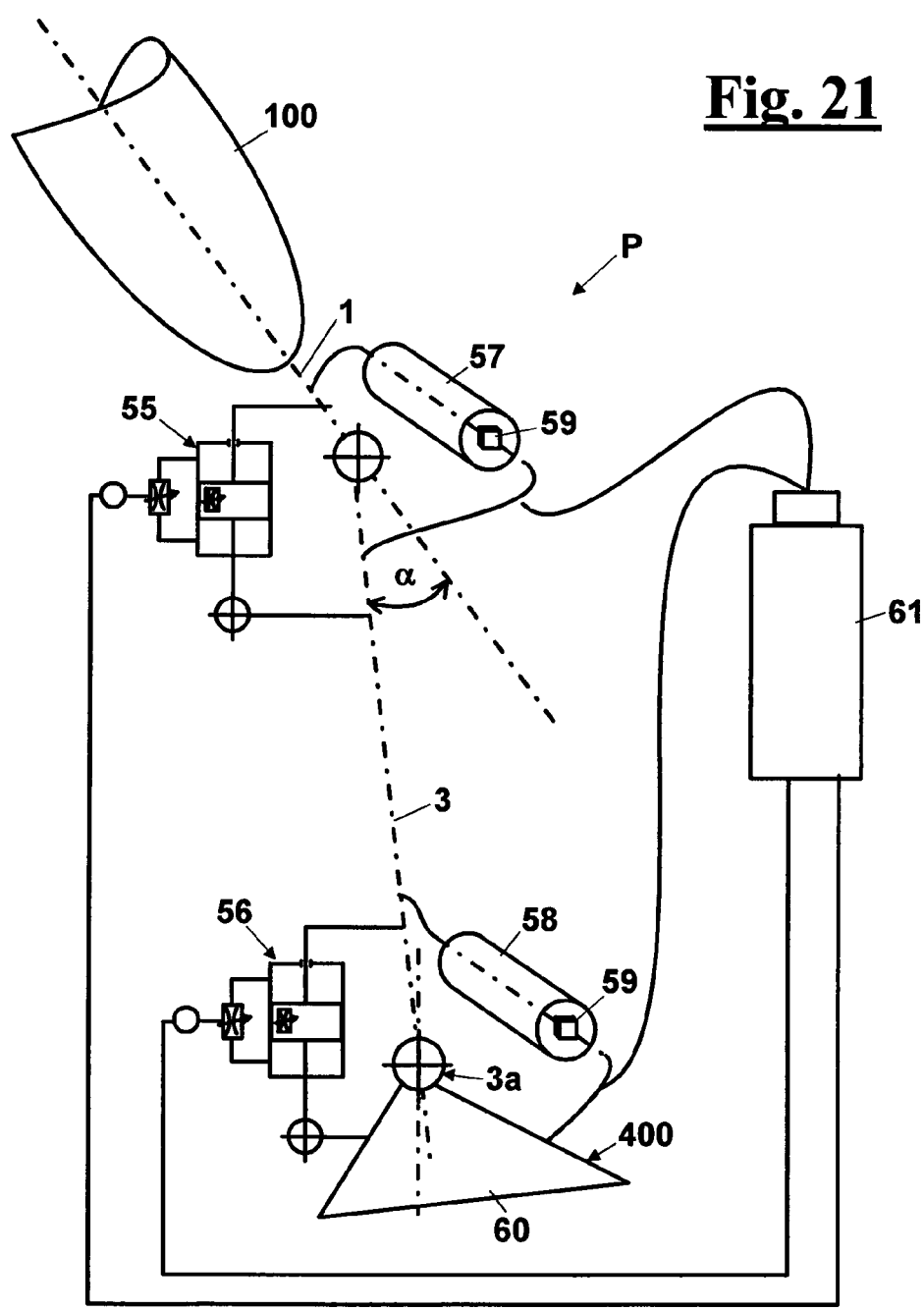
FIG. 21, shows diagrammatically the system with fluidic shock absorbers and electric motors controlled by load cells and pressure transducers connected in turn to an energy accumulator.

FIG. 21, shows diagrammatically a possible embodiment of the invention on an above knee prosthesis P, comprising hydraulic dampers 55 and 56, electric motors 57 and 58, applied respectively between femoral segment 1 and tibia 3 and between tibia 3 and foot 400. In particular, the electric motors 57 and 58 have respective position transducers 59, for example encoders, and provide a torque during the gait, as needed. Furthermore, in FIG. 21 a load transducer 60 and an energy recovery device 61 are shown, to which the two hydraulic dampers 55 and 56 are connected. During the dissipative steps, in particular, in the movement of the articulation axis 2, the energy surplus can be accumulated in the device 61. In analogy to articulation axis 2, the ankle 3a can absorb energy through the device of recovery 61 for carrying out the active steps.

Figure 22:
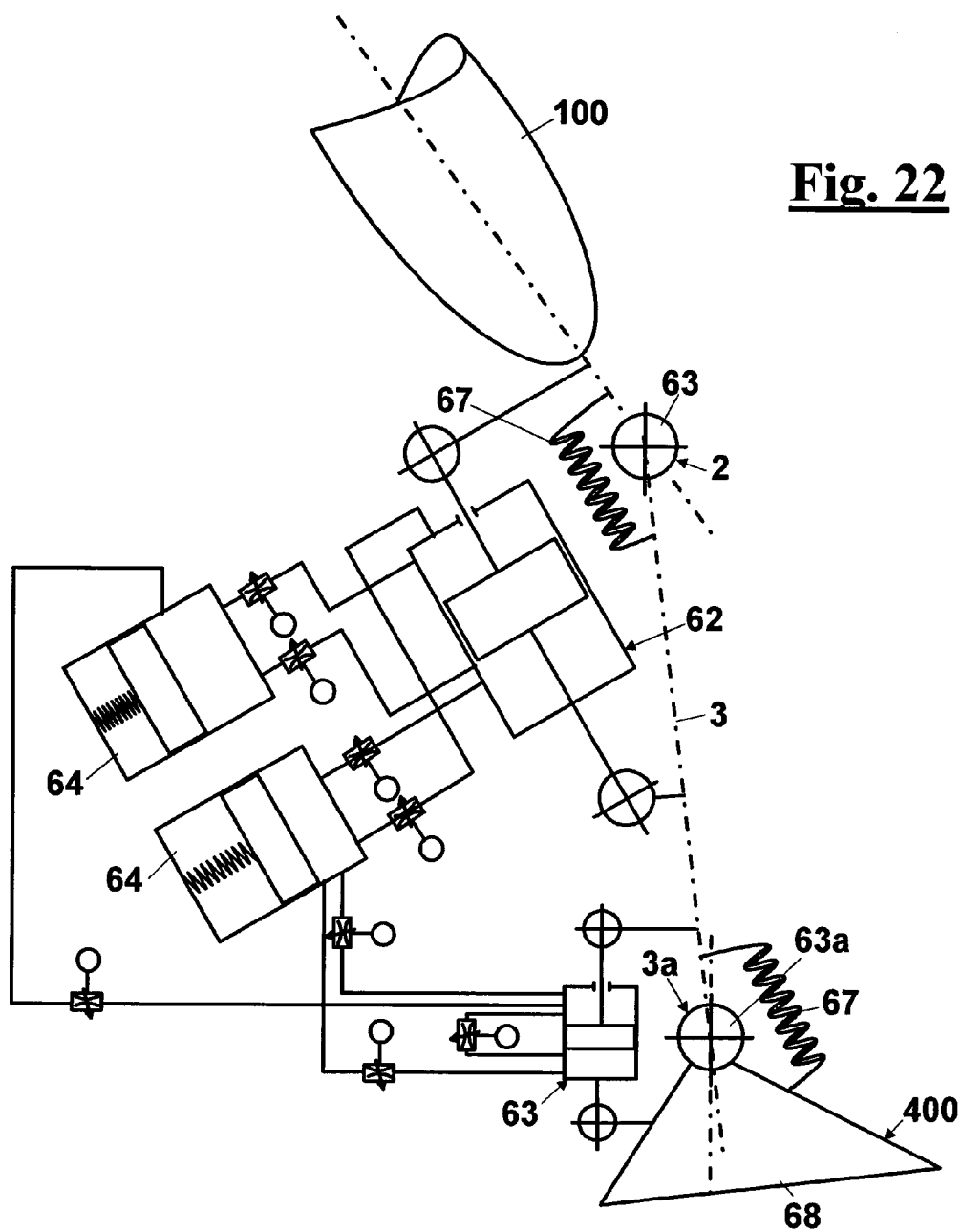
FIG. 22 shows the hydraulic system, in a possible exemplary embodiment, having spring mechanical accumulators.

FIG. 22 shows diagrammatically an above knee prosthesis P comprising a energy storage device by means of a spring. Figure shows, in particular, hydraulic unit 63 and 63a connected to spring accumulators 64. Furthermore, the above knee prosthesis P has preloading springs 67 that act in parallel to the hydraulic unit 62 in a relative damping between femoral segment 100, tibia 3 and foot 400. In FIG. 22 are then shown position transducers 63 applied to articulation axis 2 and to ankle 3a that are interfaced with the load cell 68, located at the foot sole 400. Such transducers are continuously monitored by the software that administers the exchange of data concerning the forces of the two systems and are relevant for determining the status of the gait.

FIG. 23 shows in particular, the arrangement of the position transducers 70 installed on foot 400 of prosthesis P. In particular, such transducers 70 are interfaced with each other measuring the position of the foot with respect to ground and changing the possible height from ground. FIG. 23A represents, in detail, the course of the angle β (in the drawing 23A corresponding to the angle visible in FIG. 16) compared with the distance from ground Δt, FIG. 23B, in the corresponding phases of the gait cycle.

Figures 24, 25:
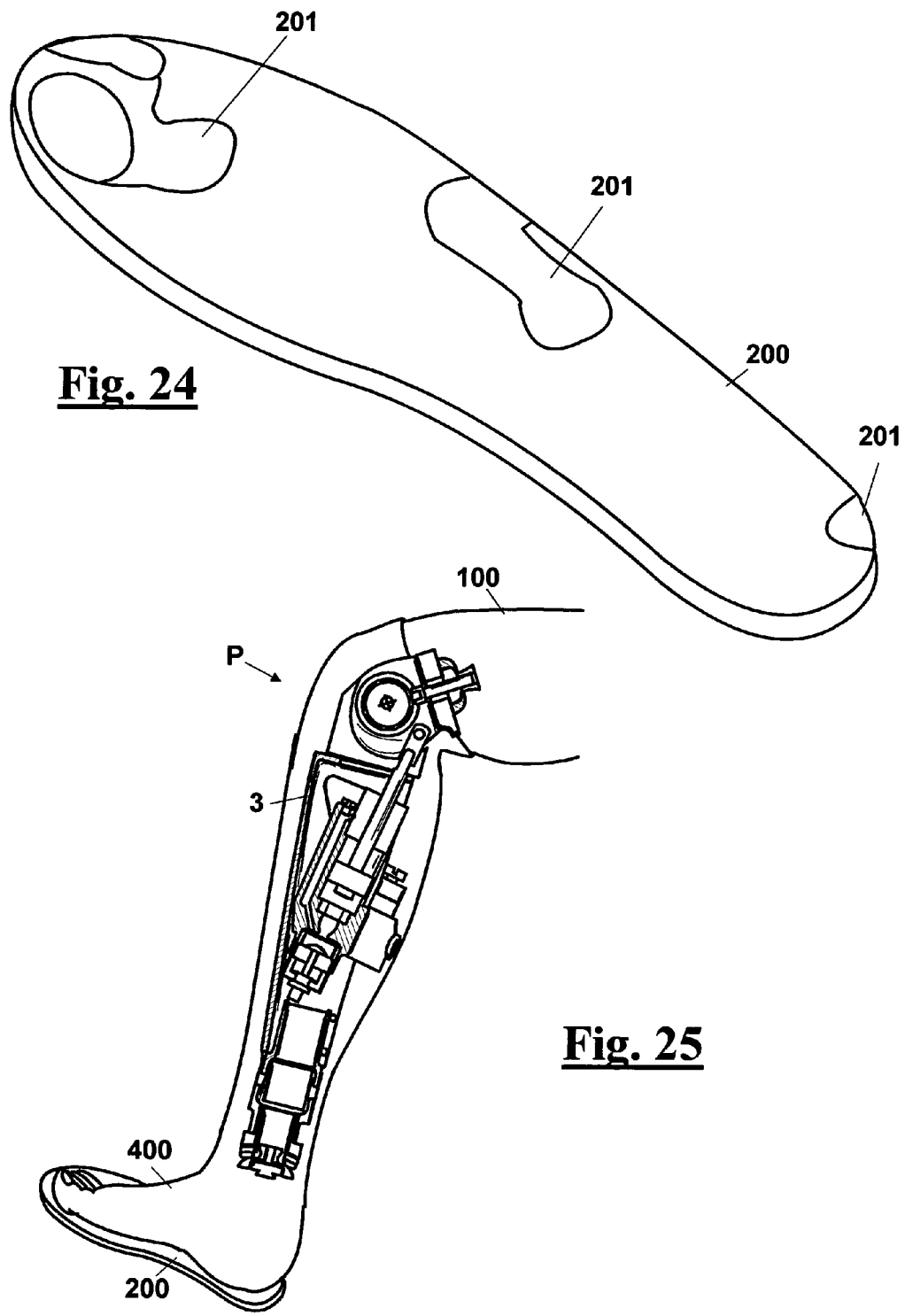
FIG. 24 shows a sensorized insole for detecting the direction of the force with respect to the ground.
FIG. 25 shows the sensorized insole of FIG. 24 applied to the foot of the above knee prosthesis.

With reference to FIG. 24, in a second particular aspect of the invention, a prosthesis is shown having the characteristic of being equipped with, at foot 400, as shown in FIG. 25, an insole having an array of force and position transducers, whose signals are computed by the microprocessor for determining the mode of interaction of foot 400 of the patient with the surroundings.

In a possible embodiment of the insole the transducers located at the insole 200, indicated as closed curves 201 allow to determine the resultant load vector, in its intensity, direction and position components, whereby the microprocessor can adjust most favourably the reaction of the damper.

In another embodiment of the insole 200 the transducers 201 located at the insole provides data on the point of application of the resultant load vector, wherein one or more force transducers are provided located in the artificial limb whose signals, computed with the signal generated by said insole, allows the microprocessor to determine the transmitted resultant load vector.

In addition, the artificial limb comprises a further transducer of the angular position located at the ankle 3a (not shown) and adapted to control the relative inclination between tibia 3 and foot 400. This information allows determining, in association to the data on the force vector provided by the insole, the position of the ankle responsive to the corresponding vector force, since necessarily the load passes through the ankle.

In FIG. 25 is shown this sensorized insole 200 applied to foot 400 of the above knee prosthesis P. In particular, the insole acquires data relative to the position of the force developed in the contact between foot 400 and the ground on which it rests. This way, it is possible to ensure with good precision proprioception of the position of prosthesis P in space and, in particular, of foot 400 with respect to the body of the user. The main object is that of knowing the point of application of the force on the ground, which is integrated, in parallel, to the intensity of the force determined through the axial force transducers.

Figure 26:
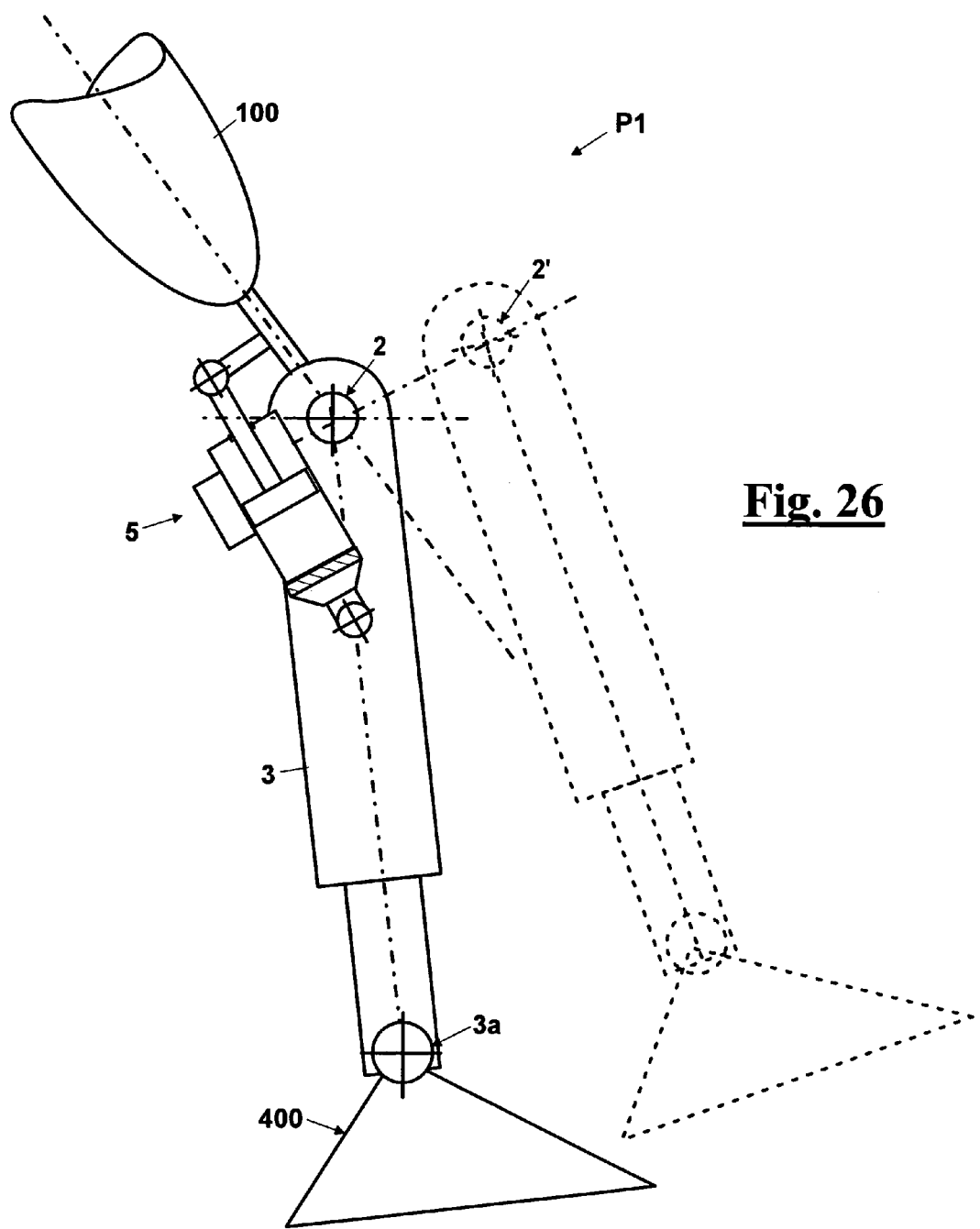
FIG. 26 shows a diagrammatical view of a prosthesis for an above-knee amputee where the hinge of the knee is in a forward position.

FIG. 26 shows an above knee prosthesis P with the articulation axis 2 in a forward position. This configuration allows a more raised position of foot 400 and is characterized by being safe owing to the braking action given by blocked damper 5.

Figure 27:
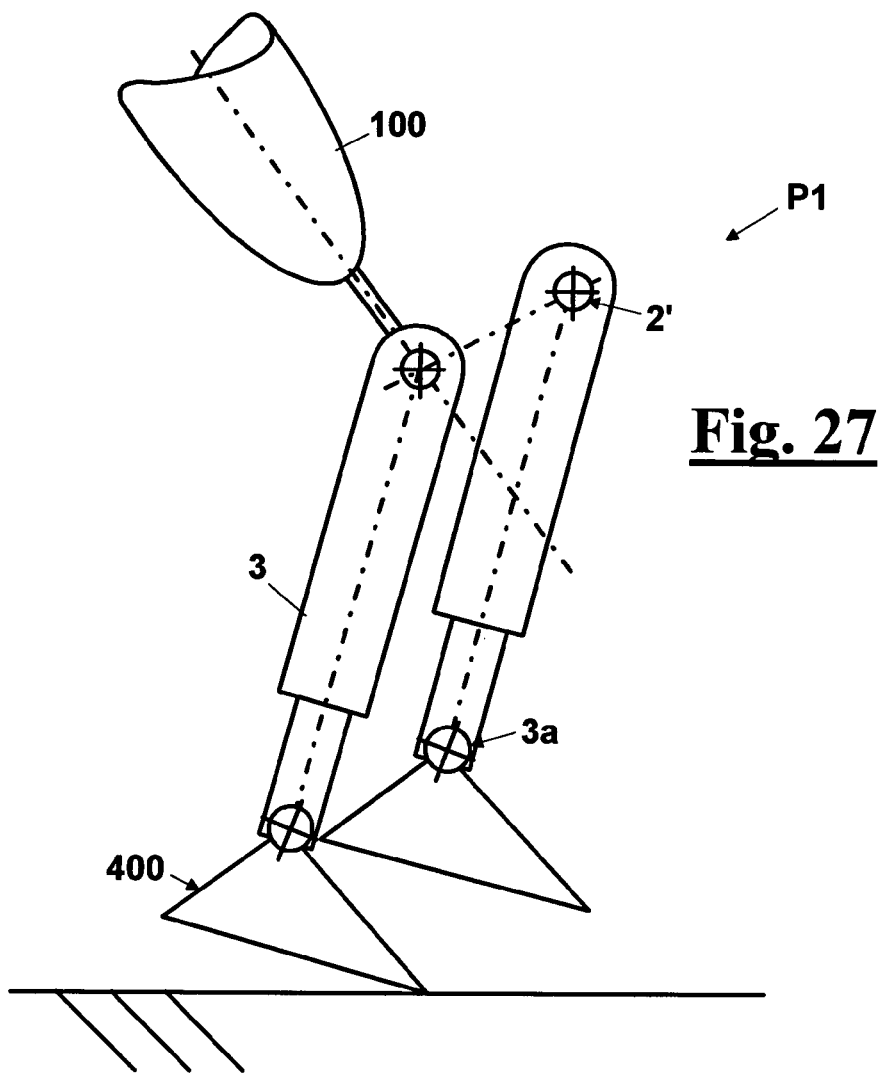
FIG. 27 shows a diagrammatical view of an above knee prosthesis with knee articulation axis arranged in a forward position and shows the advantages that such a prosthesis has in the so called Toe Clearance phase of FIG. 25.
Figure 27A:
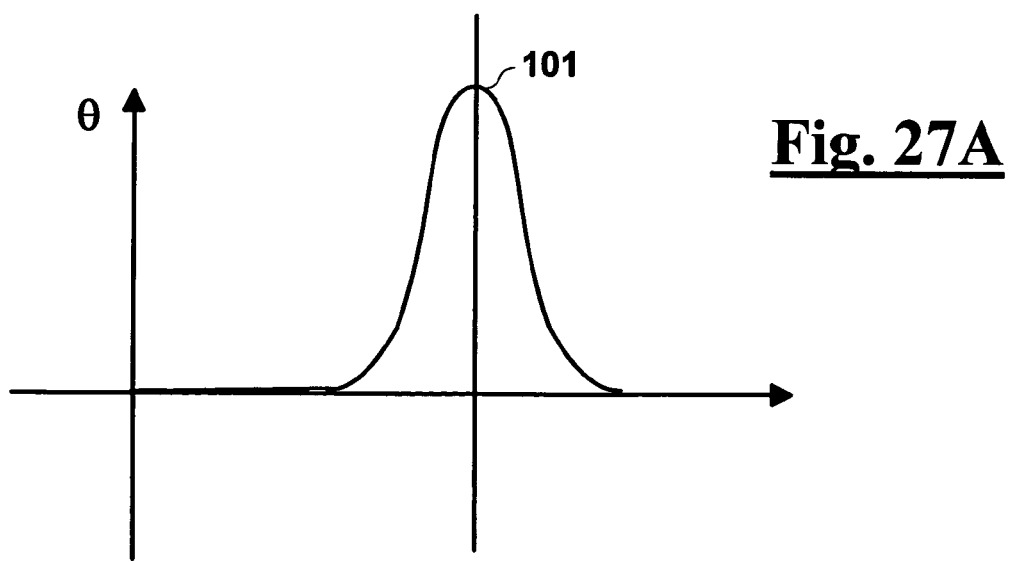

In case of the swing visible in FIG. 27 the position described of the IRC recovers space with respect to the ground as shown in the graphic representation of FIG. 27A, where the peak value 101 corresponds to a maximum angle formed between femoral segment 1 and tibial segment 3 (visible in FIG. 19). In particular, since the phase of Toe Clearance corresponds approximately to the maximum relative angle between femoral segment 1 and tibia 3, an anticipated position of the articulation axis 2' ensures some mm of clearance with respect to the ground. Specifically, with an angle of 20° of the femur with respect to a vertical direction, it is possible to have a clearance with respect to the ground of 0.35 mm for each mm of forward movement of the articulation axis 2'. A forward movement of 1 cm is equivalent approximately to a recovery of 3.5 mm, clearance from the ground, 2 cm are equivalent 7 mm from the ground.

Figure 28:
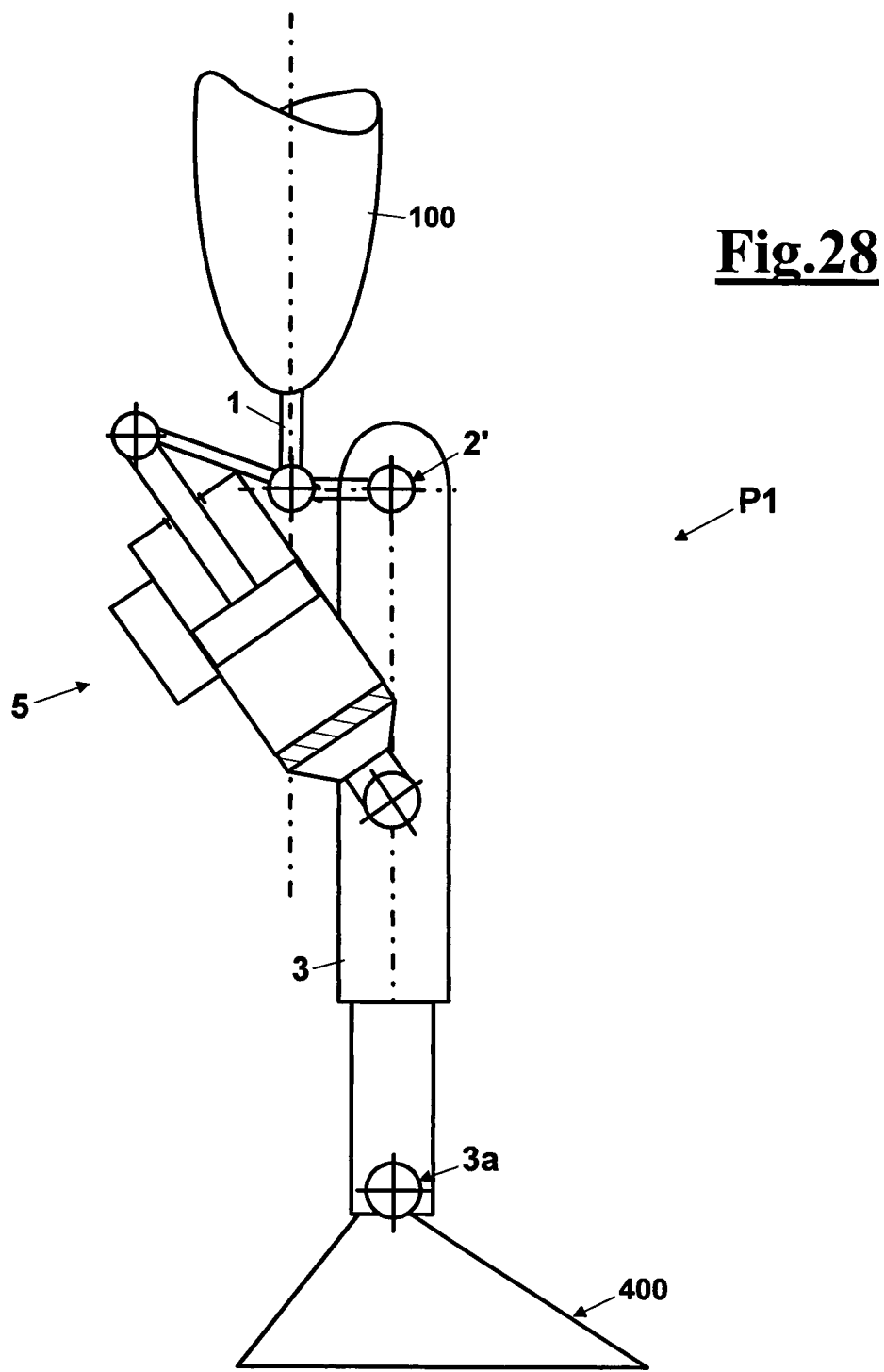
FIG. 28 shows a diagrammatical view of an above knee prosthesis with knee articulation axis arranged in a forward position when the prosthesis is orthogonal with respect to the ground.

FIG. 28, according to an exemplary embodiment of the invention, represents diagrammatically a prosthesis P1 with axis of the femur 100 orthogonal to the ground. FIG. 28 shows the position of the articulation axis 2' and the different arrangement of damper 5 in prosthesis P1. In particular, the unsteadiness of prosthesis P1, owing to the position of the articulation axis 2' is compensated by the safety supplied by damper 5 in the phases of gait.

Figure 29:
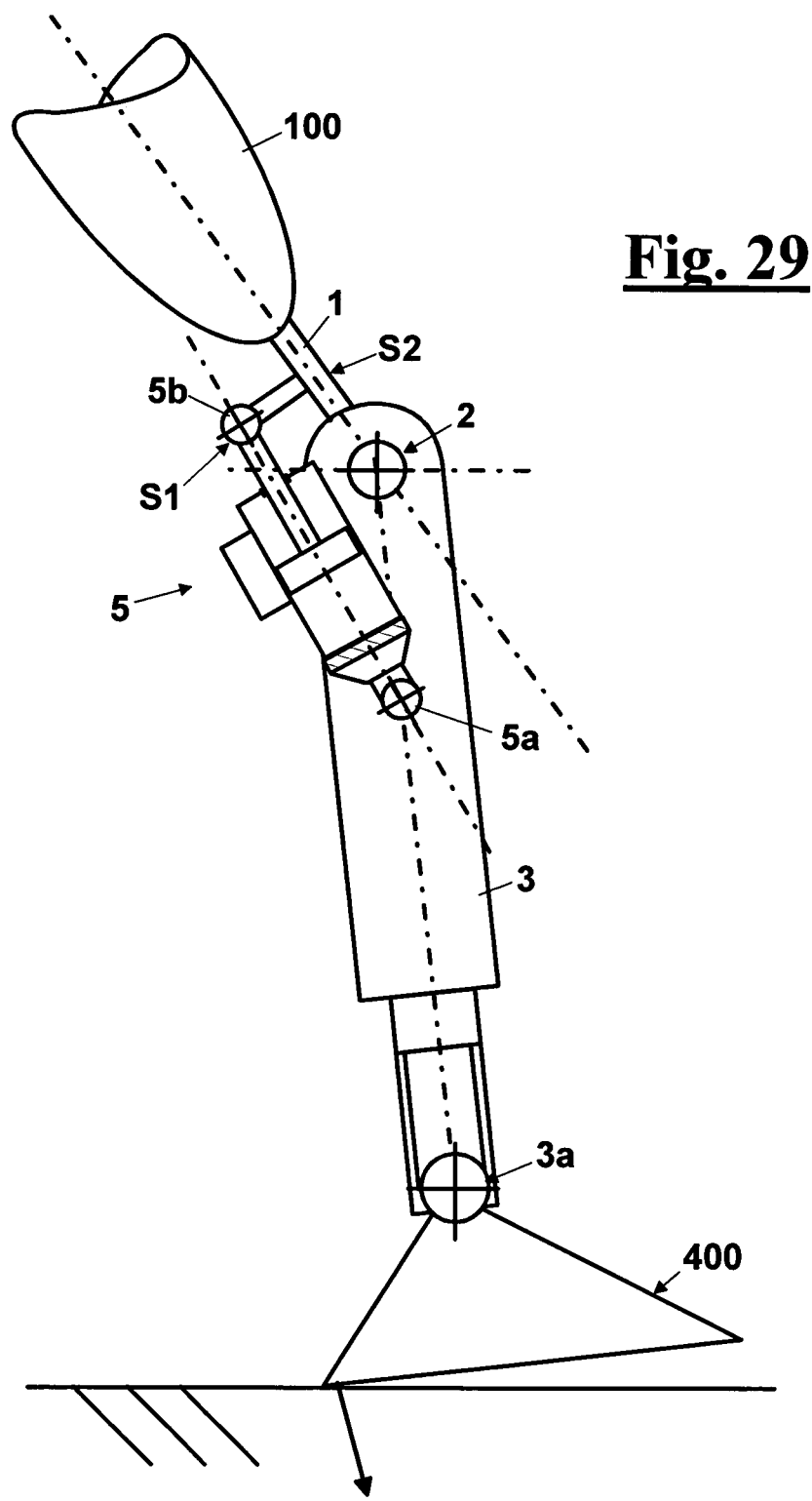
FIG. 29 shows the position of transducers on the femoral segment and on the damper and the direction of the vector force with respect to the ground.

With reference to FIG. 29 the above knee prosthesis P, in particular according to the first particular aspect of the invention, is shown. The prosthesis has a force transducer S1 located at damper 5, and the microprocessor receives a force signal by the force transducer S1 and operates the means for adjusting the reaction of the damper responsive to the detected force signal on the damper.

In particular, the force transducer S1 is arranged on the fastening the stem, alternatively to what shown in FIG. 10.

Alternatively, the force transducer on the damper is a load cell arranged on lower hinge 5a of damper 5. This way it is possible an instant verification of the status of the load on the damper and a feedback control on the dynamic behaviour of the knee.

According to an advantageous exemplary embodiment, alternatively, or in addition, a further force transducer S2 on femoral segment 1 (FIG. 29) is provided so that the microprocessor receives a force signal from the transducer S2 on femoral segment 1 and operates the means for adjusting the reaction of damper 5 responsive to the detected force signal on femoral segment 1.

In an advantageous embodiment, the force transducer S2 on femoral segment 1 comprises a first force transducer adapted to measure the action on the femur 100 according to a direction longitudinal to the femur, and a second force transducer adapted to measure the action on the femur in a direction orthogonal to the femur. This way, the overall force information on femur 100 and on damper 5 is capable of determining satisfactorily the tensional status in the artificial limb.

In an exemplary simplified embodiment, the second force transducer on the femur 100 provides only the sign of the force on the femur in a direction orthogonal to the same.

Furthermore, a position transducer can be provided at the articulation axis 2 that reproduces the knee movements, the position transducer measures, thus, the rotation of the knee.

In a particular embodiment, the operation provides that femoral segment 1 and tibial segment 3 are located, at the beginning of a phase at the end of the swing, which is the phase of maximum extension of the movement, in a condition of singularity measured by a mechanical abutment integrated in the damper. This way, the force transducer S1 on damper 5 measures the actual load transmitted to the articulation also in the condition of singularity and the microprocessor that computes the measure can discriminate and control this phase during the gait.

FIG. 30 shows, in a fifth particular aspect of the invention, a motor on the knee articulation capable of allowing in any case to the patient a swinging action, or swing. In a first possible embodiment this is obtained with a reduction gear 92 mounted on the motor 91 and have a fast shaft (not shown) connected to the electric motor 91 and a slow shaft 93 connected to the knee articulation. The motor 91 supplied by a current whose intensity is adjusted by the microprocessor (not shown) to obtain a torque at the articulation axis similar to that obtainable by a hydraulic damper. An encoder 90 transmits to the microprocessor the rpm of the motor. On the slow shaft 93 an output shaft 95 is mounted with a measurement system of the backlash.

In particular, the angular position of the motor 91 is continuously determined by an encoder 90. The angular position of the slow shaft 95 is continuously determined by a second encoder or by a Hall effect sensor 94 having a magnet. This way, it is possible to driving the servomotor in order to accumulate the backlash present in the kinematical chain at the desired speed of rotation, for example concordant or discordant with the moment transmitted and depending on the forward or backward movement of the gear motor; this way, it is possible to minimize the amount of energy dissipated in the backward movement that is characterised by less efficiency than the forward movement, and maximizing then the use of the kinetic energy and the energy recovery in the accumulator.

Similarly, in a way not shown but in a way similar to the gear motor for knee, a second gear motor can be provided connected to the ankle articulation controlled by the microprocessor in order to obtain a torque similar to a hydraulic damper.

In a way not shown, the reduction gear, located at the knee articulation, has a fast shaft connected to the electric motor and a slow shaft connected to the articulation that are orthogonal to each other, to achieve a reduced encumbrance as far as possible similar to the anatomic sizes. In a similar way, the artificial limb provides a second gear motor having orthogonal axes and connected to the slow shaft at the ankle articulation.

Alternatively, located at the knee articulation and the articulation of the ankle a freewheel is located (FIG. 31, 31A) adapted to free the tibia from the reduction gear during the swing phase, i.e. caused by the inertia of the leg, vice-versa the freewheel constrains the two movements to each other when the motor/brake has to act on the tibia. A further exemplary embodiment not shown provides that on the freewheel, on the shafts of the reduction gear, two angular transducers are applied adapted to measure the angular position of the shafts.

An exemplary alternative structure, equivalent to the previous, provides one or more moment transducers at the transducers angular.

Figure 32:
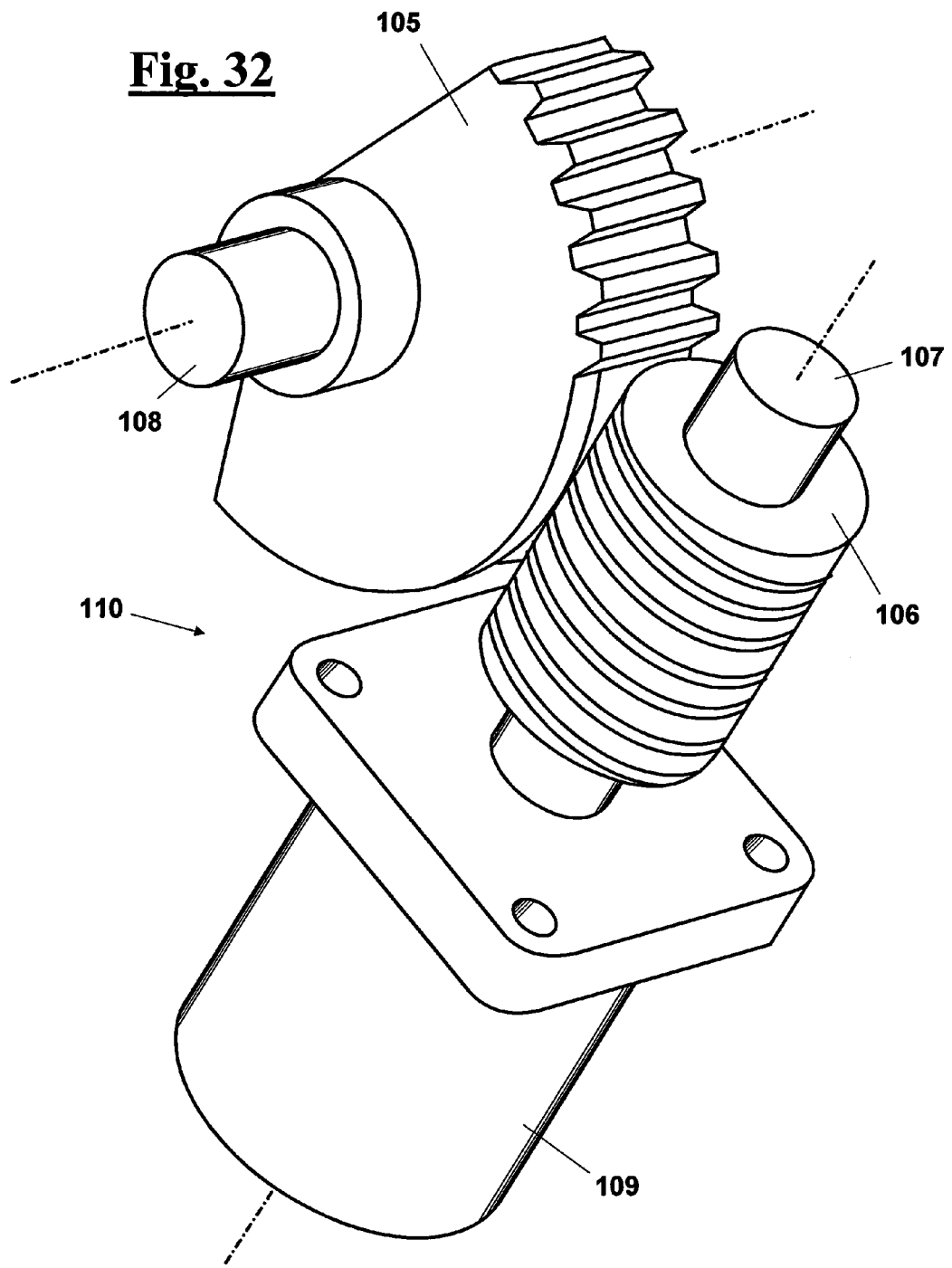
FIG. 32 shows a gear motor of worm drive type in a simplified configuration of operation.

FIG. 32 shows a gear motor 110 of worm drive type. In particular, the wheel 105 has a gear ratio between the fast shaft 107 and the slow shaft 108 higher or equal to 5.

On the quick shaft 107, in particular, a first position transducer is applied (not shown) to determine the instant position of the same; on the slow shaft 108 a second position transducer is mounted (not shown). This way the motor 109 drives the fast shaft 107 in order to maintain a predetermined play with the slow shaft 108 and to allow the reversibility of the motion.

Figure 33:
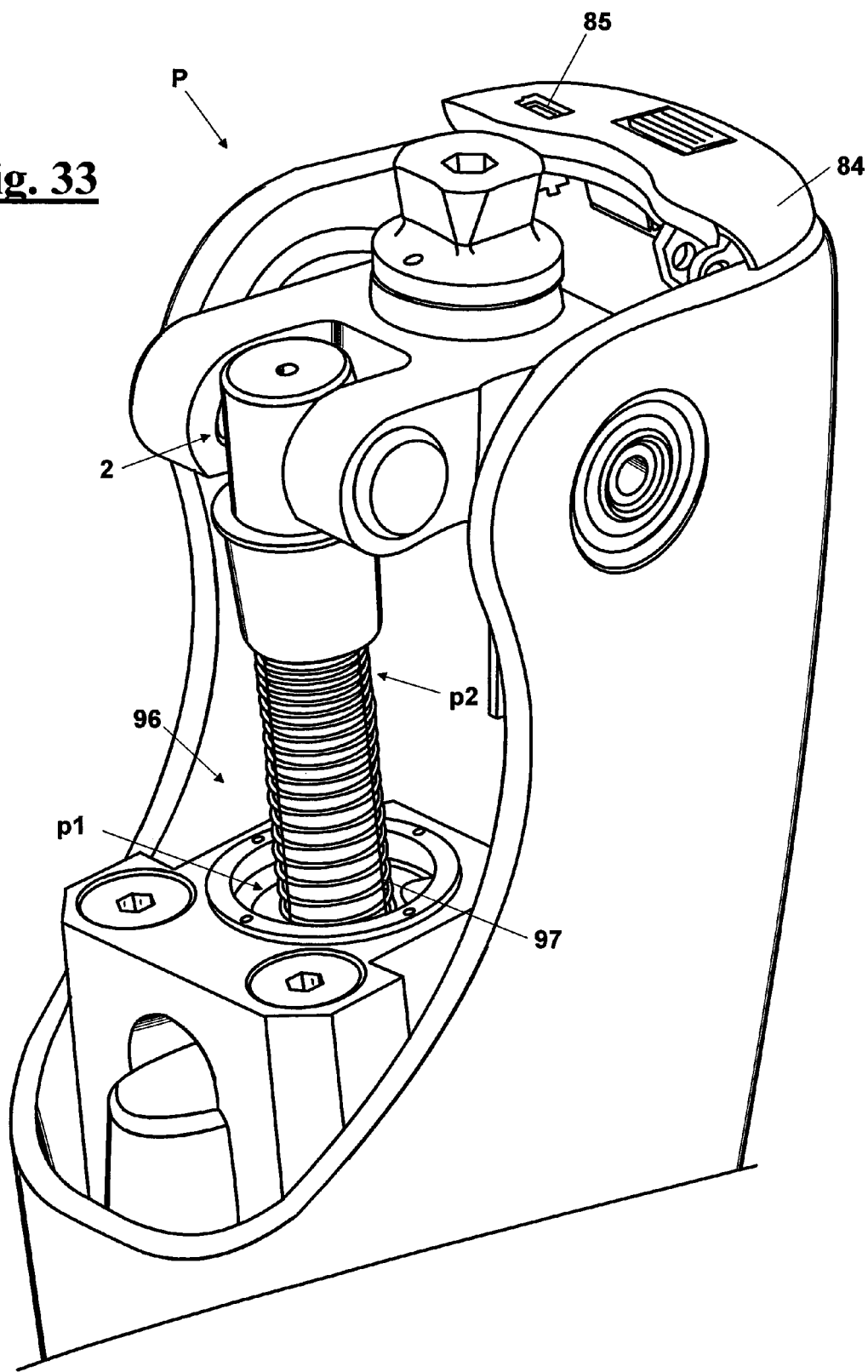
FIG. 33 shows a motor having variable pitch springs that allow to achieve optimal stiffness in various configurations for reducing the energy consumption of the prosthesis.

FIG. 33 shows another exemplary embodiment of the brake/motor device 96 on the knee articulation 2. The object is of assuring a correct position of femoral segment 100 with respect to tibial segment 3 in all the gait conditions, in particular at low speed.

In particular, the motor 96 intervenes assuring the correct realignment of tibia 3 if the patient, in particular a new amputee or a elder person, has hesitations during the gait.

According to the operation of this solution, for reducing the energy consumption of prosthesis P, and increasing the range of the motor/generator system 96, variable pitch springs 97 are provided that allow to achieve an ideal stiffness, i.e. low stiffness for small angular travel between femoral segment 100 and tibial segment 3, and high stiffness for large angular travel.

In particular, variable pitch springs 97 are helical springs having a diameter and a first pitch $P_1$ at one end and a second pitch $P_2$ at the opposite end in order to obtain a continuous transition of the stiffness between a first value $K_1$ and a second value $K_2$.

Figure 34:
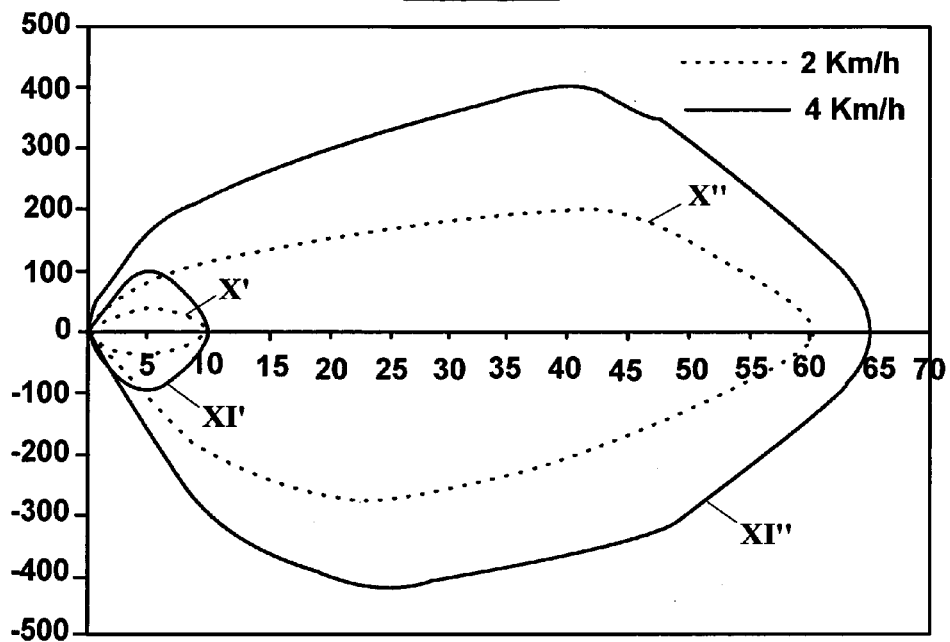
FIG. 34 shows a graphic diagram that reproduces the phases of the gait cycle, respectively at 2 and at 4 km/h.

FIG. 34 shows, according to the fourth particular aspect of the invention, a graphic diagram that reproduces the movement of the artificial limb, for adjusting the pace of the gait in a same gait cycle. In particular, FIG. 34 shows a case of walking on a plane ground, is defined by a family of similar curves having different amplitude responsive to the average walking speed. The curves comprise the trajectory of tibia 3 with respect to time described by the angle tibia-femur and by its derivatives with respect to time.

More precisely, for a measured speed, an ideal curve that describes a gait comprises two sub-curves, a smaller inner curve X', corresponding to the stance phase, and a larger external curve X", always corresponding in part to the stance phase, at least for part in the first quadrant.

Both curve pass through the origin. Versus the speed of the gait the curves change shape, describing wider trajectories with an increase of the speed of the gait, respectively depicted by the corresponding curves XI', XI". In particular, the relative speed of the gait are 2 and 4 km/h, respectively for curves X', X" and XI', XI".

Then, since each curve defines an ideal gait cycle for a measured speed, and the curve changes its shape versus the gait speed, and each curve has a corresponding parameter, once detected a change of the speed within a gait cycle, it is possible to cause tibia 3 to follow a curve corresponding in that phase of the gait cycle, but for a new speed. This way, by recognizing quickly the need of the amputee to change the speed of the gait, it is possible to cause the prosthesis to follow a curve of different amplitude with respect to that followed previously.

The typical operations of stopping from walking, sitting down and standing up can be defined in turn by special families of curves. Similarly, walking uphill, downhill, going down and up the stairs, pedaling on a bicycle, and, in general, other possible conditions of movement, can be represented, in general in a n-dimensional space, by a characteristic curve.

It is possible to increase the parameters defining the curve, and in a possible configuration of the space, exemplifying and not limitative, the coordinates are five:
time;
relative rotation angle between tibia and femur;
first derivative with respect to time for said angle;
algebraic value of the resultant load vector transmitted to the ground;
algebraic value, with respect to the axis of rotation of the articulation, of the moment of the resulting from.

It is possible to put further parameters, such as the second derivative of the angle, for representing in a more complete and generalized way the different possible gait conditions; or it is possible to reduce the number of coordinates to obtain a simplified but rougher representation.

In addition, further transducer means are provided adapted to measure continuously with respect to time, or at discrete time intervals, the parameters that represent the coordinates of the space. In particular, at least one memory unit is provided, such as a RAM, ROM, EPROM etc. adapted to memorize the characteristic data of the curve X', X" and XI', XI" and to memorize the data determined by the transducers with respect to time.

Furthermore, a microprocessor is provided adapted to analyse the data determined by the transducers, comparing them with the data recorded in the memory unit, for determining, among the recorded data, the curve that is most suitable for representing the actual gait, called ideal curve.

This way, the microprocessor adjusts the reaction of the damper for minimizing the error definable as the distance, in an n-dimensional space, between the actual point, whose coordinates are the measurements made by the transducers, and the corresponding point of the ideal curve. Furthermore, the microprocessor ascertains, according to the error, to the ideal curve used and to the family of curves, if it is useful to continue on the actual ideal curve, or if it is better to use a different ideal curve or to change family of curves.

This architecture of control is capable, thus, of optimize the gait responsive to the evolution of the psychophysical conditions of the patient, therefore the patient walks always at best both just after the amputation, when hesitation for the gait is high, and when the amputee has acquired more confidence. A further advantage is that the time for rehabilitation is reduced, since the patient is continuously assisted by a device that carries out the function of electronic rehabilitating device suitable for correcting and improving the gait.

Another possible exemplary embodiment provides measuring the moment of the femur at the articulation, and in this case, and without limiting the scope of the invention, the coordinates of the space are the following:
time;
relative rotation angle between tibia and femur;
first derivative with respect to time for said angle;
longitudinal force acting on the damper;
moment transmitted by the femur to the articulation.

The latter parameter allows detecting indirectly the wishes of the patient, because these are evidenced by the moment that the stump produces on the articulation.

Figure 35:
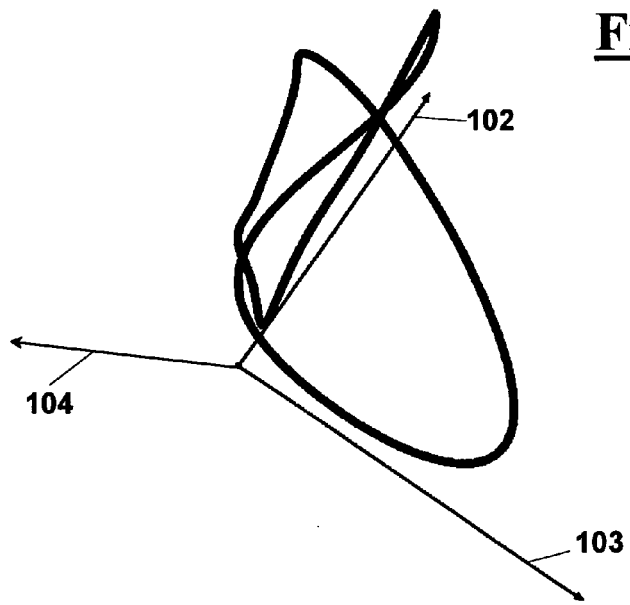
FIG. 35 shows, in a three-dimensional simplified representation, curves that identify respectively the tibia-femur rotation angle, the first derivative with respect to time for the tibia-femur rotation angle and the force acting on the damper.

FIG. 35 shows a curve that defines an ideal gait cycle for a determined average speed. With respect to the average speed the curve changes its amplitude, but the curve shape is the same. Then a family of similar curves, described in a three-dimensional space, like that of FIG. 35, identifies univocally walking on a plane ground and a parameter, such as the average speed, discriminates the curves of the family from one another.

Figure 35A:
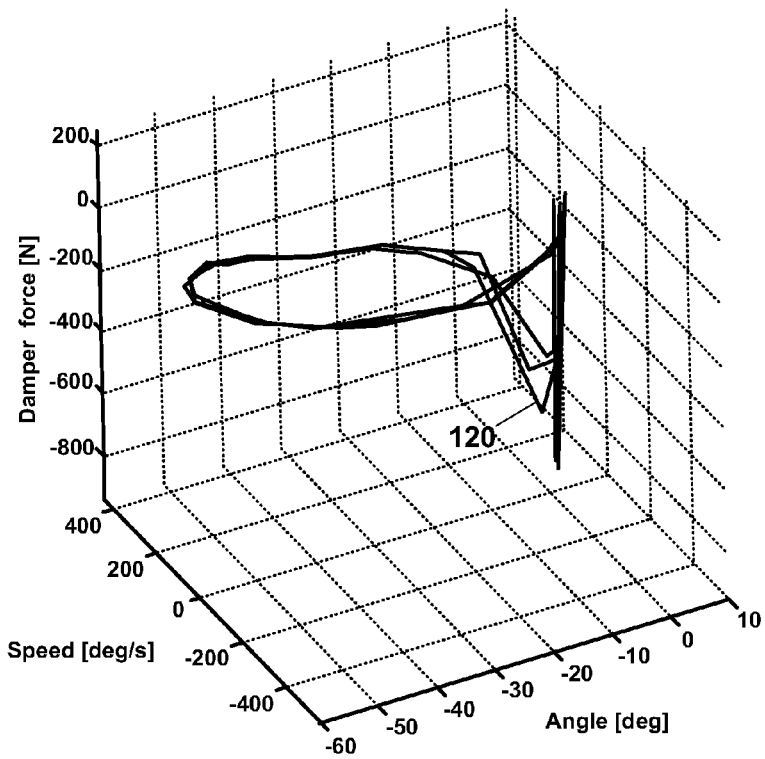
FIG. 35A shows in addition a three-dimensional curve where each curve represents a gait different from a model of reference.

FIG. 35A shows, instead, a plurality of three-dimensional curves used, in particular, as reference for controlling and for adjusting the swing phase. The present figure highlights a curve 120 which distinguishes from the model of reference. In this case, the reason could be a wrong gait of the patient that hits against an obstacle or stumbles during the gait.

In the present simplified configuration, the coordinates of the space are three: tibia-femur rotation angle 102, first derivative with respect to time for the tibia-femur rotation angle 103 and force acting on the damper 104, orthogonally to the plane containing the two axes 102 and 103.

Without limiting the scope of the invention, the need of accelerating the gait on a plane ground causes a variation of moment and/or force orthogonally to the femur. The same occurs when the patient wishes to decelerate.

The control system, acquiring the values of these parameters that are correlated to the need of the patient, is capable to adjust the behaviour of the artificial limb to ensure a very quick response to follow the wishes of the patient, about substantially instantaneously. This control system is suitable especially for those patients that need a high dynamism. In general it recovers, at least partially, proprioception of the missing limb since a direct relationship is established between the wishes of the patient, (for example the pressure of the fastening of the prosthesis on the skin of the stump) action and perception.

Alternatively, the means for defining the gait conditions are of matrix type.

Figure 35B:
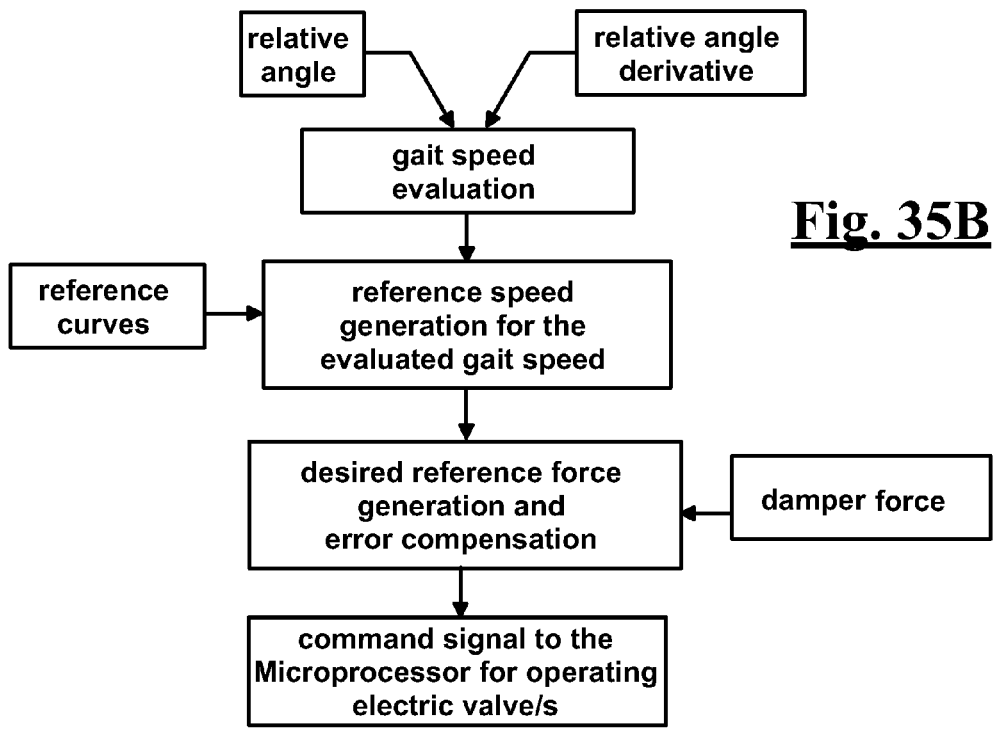
FIG. 35B shows a flow-sheet of the main phases followed by the microprocessor in the operation and control of the gait.

FIG. 35B shows a flow-sheet of a loop of control and operation of the gait mounted on the prosthesis. In particular, after the input of data such as, for example, angle of the articulation and first derivative thereof, estimation is calculated of the speed of the gait. At the same time, the program recalls from a memory the reference curves. Then, there the speed of reference obtained integrating the chosen reference curve is obtained. This way, in the successive gait cycle, a corresponding reference of force and compensation of the error are obtained through an input and output of the force applied on the damper. As final step, a command signal is sent for adjusting the oil flow by the respective solenoid valves. If the hydraulic circuit of the prosthesis is that of FIG. 6. Vice-versa, the command signal is sent only to the solenoid valve in the case of FIG. 6A with geometric adjustment of the extension phase.

Figure 37:
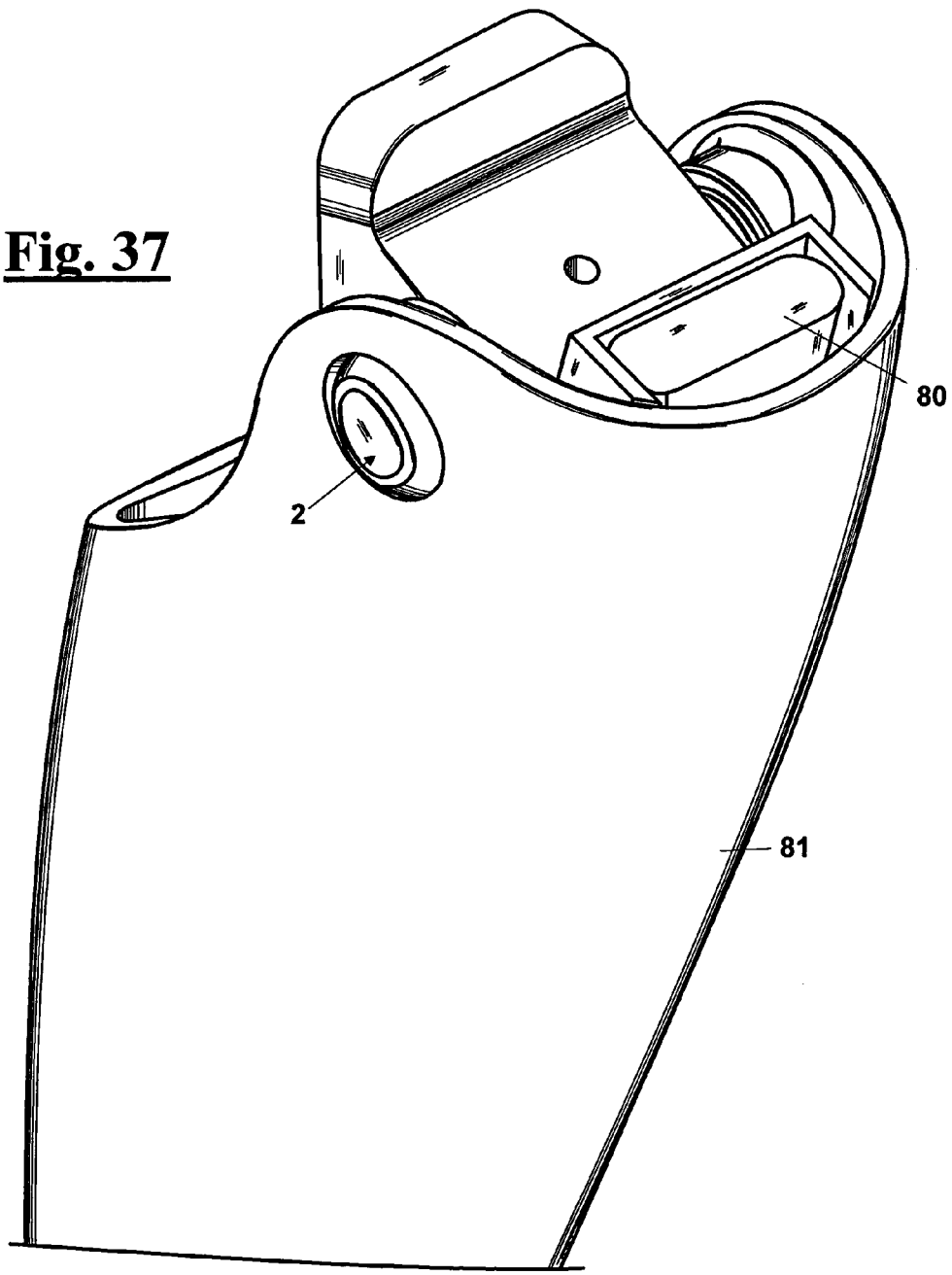
FIG. 37 shows the energy storage unit, of FIG. 36, with a respective protection element.

FIGS. 36 and 37 show a view, in a sixth particular aspect of the invention, of the electronic devices that are arranged in the artificial limb, both in the case of only the knee articulation and in the case of the latter in combination with the ankle articulation, fed by a rechargeable battery 80, for example of the type with lithium ions, replaceable quickly and autonomously by the same patient that can wear the artificial limb when replacing the batteries.

A special device, for example an acoustic alarm (not shown), signals to the patient when battery 80 on the artificial limb is going to be flat. The patient can, thus, easily replace it with a second battery that has been brought with; This way, the range of the prosthesis is longer.

The number of charged batteries that the patient carries with can be naturally larger than two, and this is advantageous for patients who like trekking, or who are accommodated, even occasionally, where electricity is not easily available, or to avoid long waits for one battery to be recharged.

Figure 40:
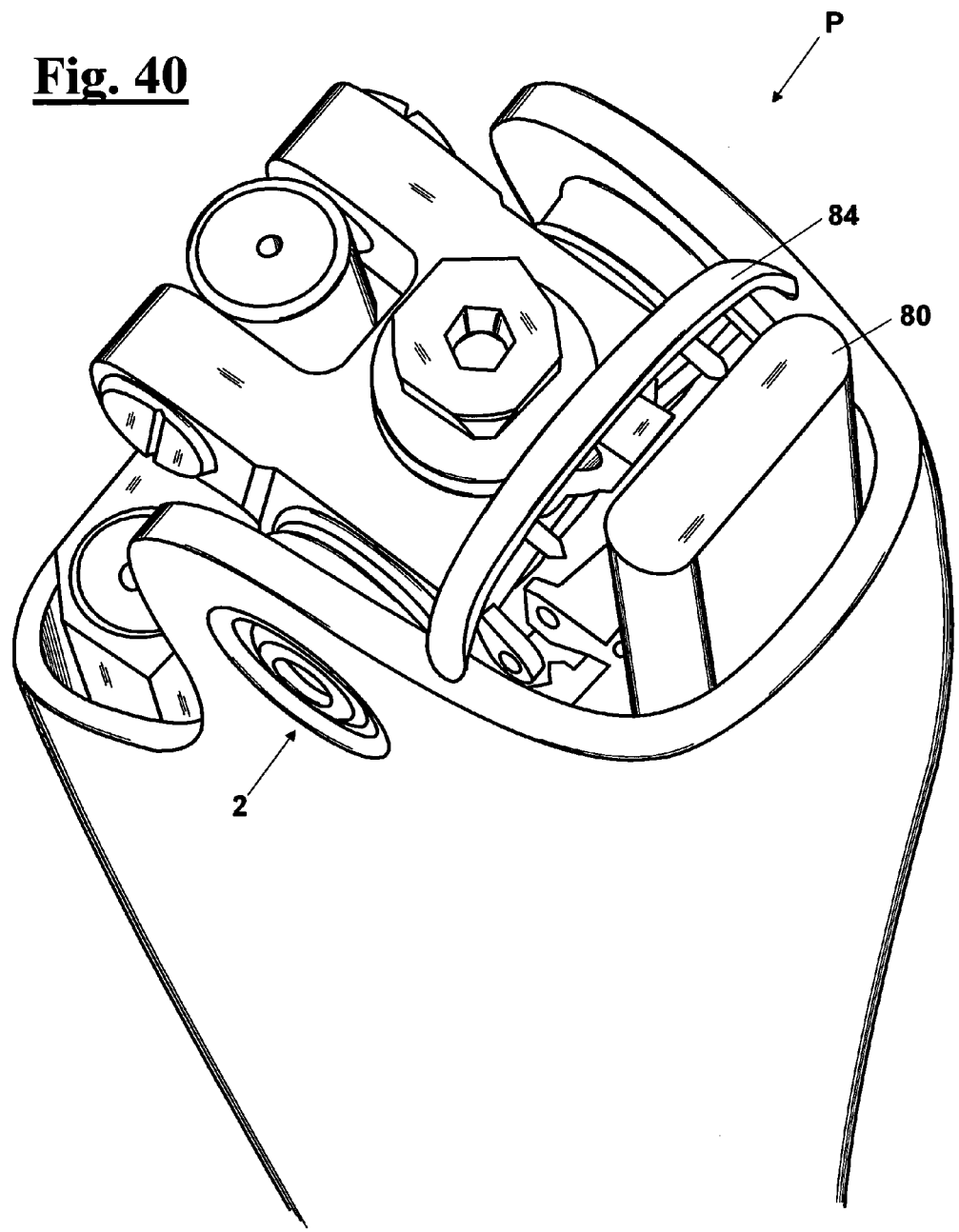
FIG. 40 shows diagrammatically the operations of extracting the battery, shown in FIG. 39, for charging and/or changing it.

Battery 80 is located at the rotula in a forward position with respect to the articulation axis 2; the patient can approach battery 80 for removing and replacing it only in safety conditions, i.e. when sitting, whereas the slot containing the battery cannot be opened in other situations (as shown in FIG. 40); therefore the arrangement in a front position of the battery allow an easy access from the above ensuring at the same time a geometry following the anatomy of the missing limb, respecting safety ergonomic conditions.

Figure 38:
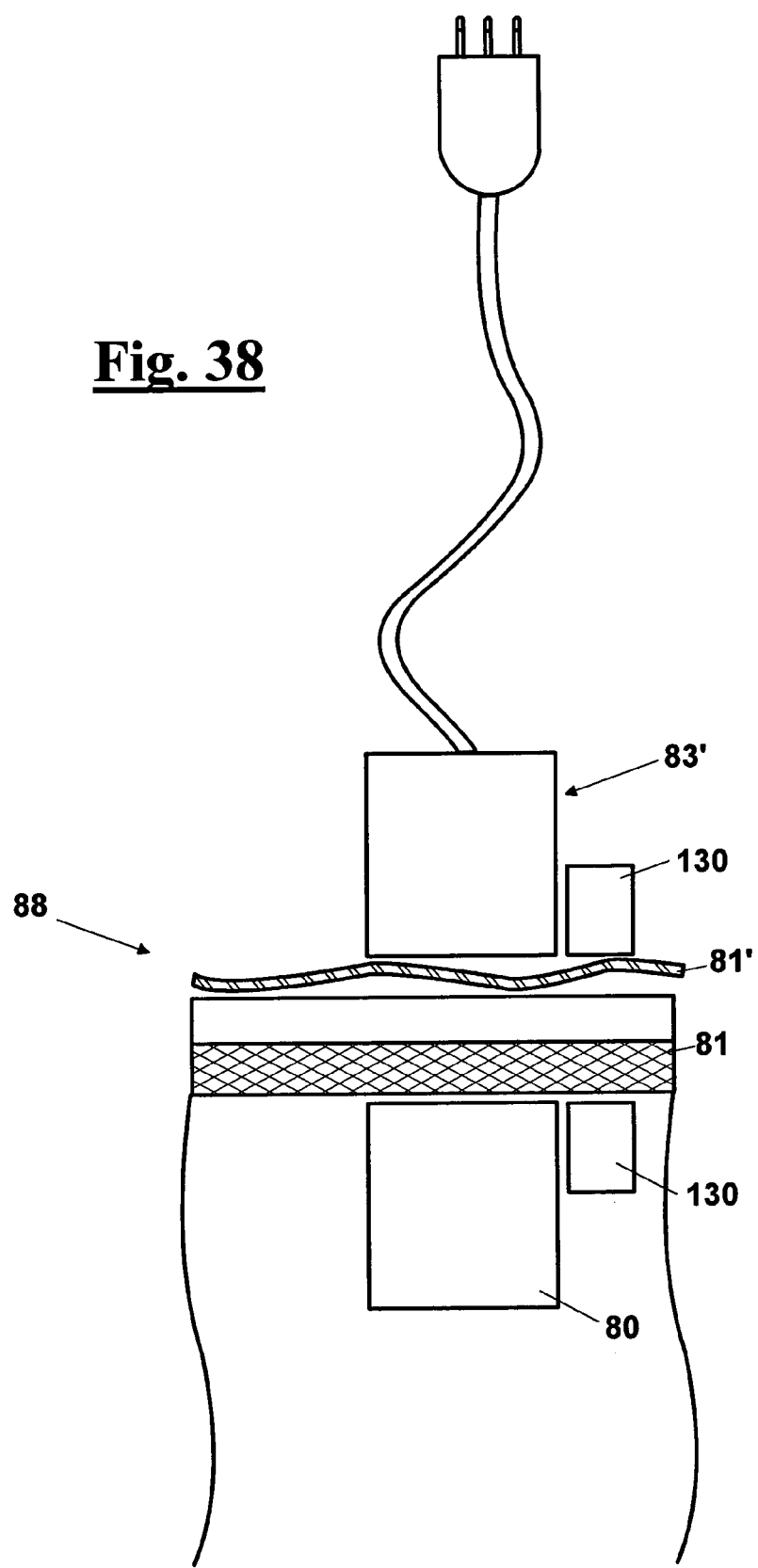
FIG. 38 shows an external battery of larger size than an inner battery and that the patient can carry for charging the latter.

In combination or alternatively, with the previous features, on the artificial limb, both in the case of only the knee articulation or in case of a combination of the latter with the ankle articulation, the devices are fed by a rechargeable battery 80, for example of the type with lithium ions, whose recharging circuit may be connected to the supply circuit 83' external to the limb by a primary/secondary connection 88 of a transformer, as shown in FIG. 38.

The recognition and the connection between the two circuits is effected by two respective magnets 130 that in use, are located coincident with each other. This way, the patient can easily recharge battery 80 while wearing the artificial limb, an aesthetic coating 81, also shown in FIG. 36, and clothes 81'.

In addition, the outer recharging circuit can be supplied in turn by a battery of larger size (not shown) that the patient can wear, for example fastened to a waistbelt, in a backpack, in a pocket etc.

Figure 39:
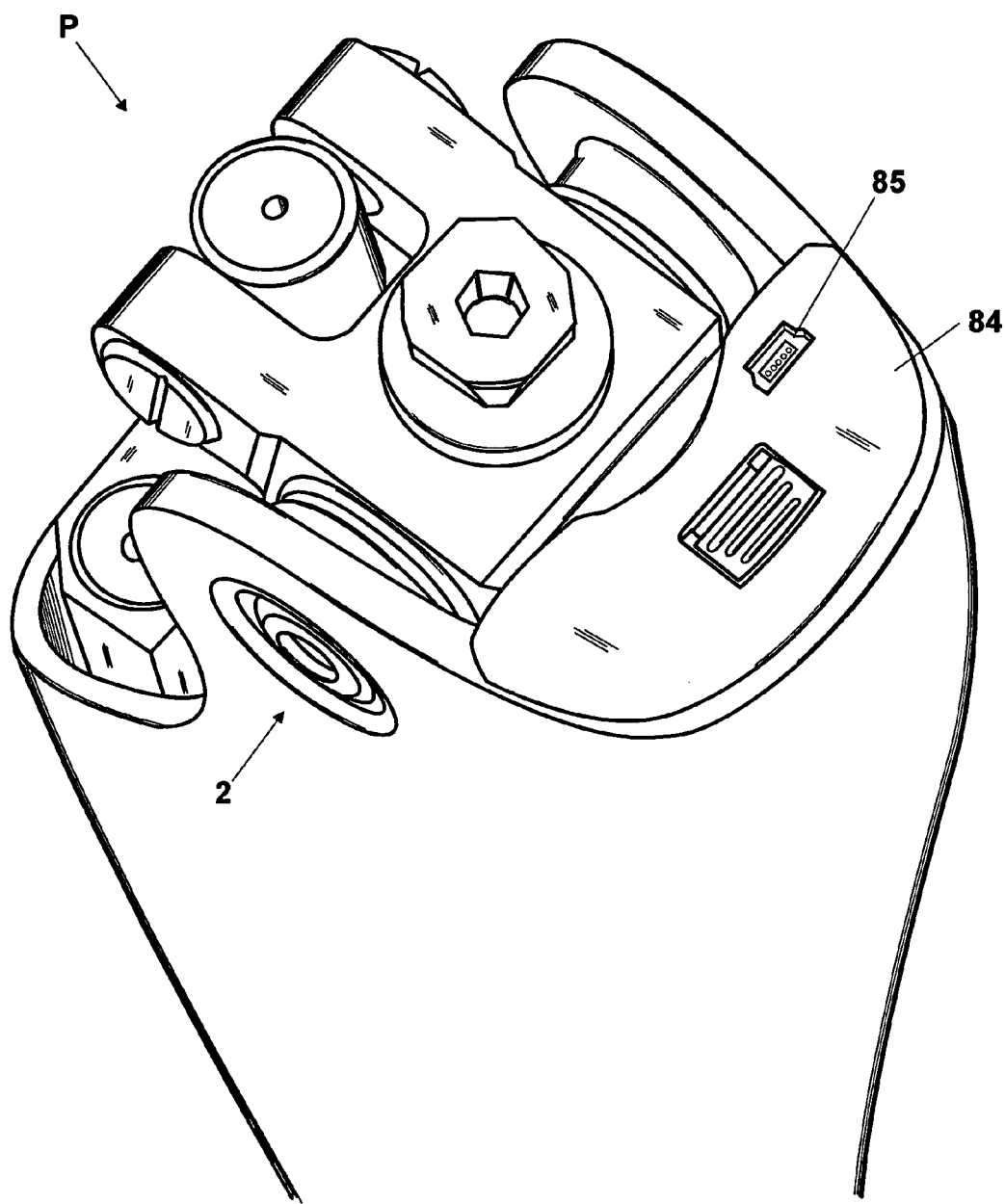
FIG. 39 shows the energy storage unit, enclosed in respective housing, having interconnection elements.

Alternatively, on the artificial limb a port is present 85, for example of USB type, shown in FIG. 39, by means of which the artificial limb P can be connected, both in the case of only the knee articulation and in the case of the latter in combination with the ankle articulation, to a computer in order to obtain, by a single link, the charge of battery 80 that feeds the electronic devices that are arranged in the artificial limb, for updating the firmware, and transferring, for a deferred analysis, the data recorded by the artificial limb to the computer.

Furthermore, special software installed on the computer or available in the network analyses the data stored in the memory of the artificial limb and programs again the firmware for improving the behaviour of the artificial limb responsive to the wishes of the patient.

FIG. 40 shows the steps of changing battery 80. In particular, they comprise simply opening a cover 84 and changing battery 80. Battery 80 is at the rotula in a forward position with respect to the articulation axis 2 and is accessible from the above by the patient who is in a sitting position, in a way congruent with the geometry of the limb, in a safety position with sitting patient.

The foregoing description of a specific embodiment will so fully reveal the invention according to the conceptual point of view, so that others, by applying current knowledge, will be able to modify and/or adapt for various applications such an embodiment without further research and without parting from the invention, and it is therefore to be understood that such adaptations and modifications will have to be considered as equivalent to the specific embodiment. The means and the materials to realise the different functions described herein could have a different nature without, for this reason, departing from the field of the invention. It is to be understood that the phraseology or terminology employed herein is for the purpose of description and not of limitation.

The invention claimed is:

1. A prosthesis for above-knee amputees, said prosthesis having a femoral segment, which can be fixed to a femoral connection, and a tibial segment pivotally connected to each other about an articulation axis that reproduces the knee movements, said tibial segment being articulated by an ankle to a foot having toes, a sole of the foot and a heel, wherein said knee movements comprise a swing phase, between bringing the toes off the ground and landing the heel, and a stance phase, comprising landing the heel, loading the sole of the foot and bringing the toes off the ground, a hydraulic damper being provided having respectively an upper hinge and a lower hinge connected respectively with said femoral segment and said tibial segment and damping the relative movement of said tibial segment with respect to said femoral segment, so that in the stance phase, the tibial segment is braked with respect to the knee articulation between said femoral segment and said tibial segment, wherein the hydraulic damper comprises a cylinder-piston and a stem connected to said piston, and a microprocessor is provided for adjusting the damping reaction of said damper;

wherein said damper is of hydraulic type and comprises blades arranged as check valve blade springs for opening an oil flow responsive to a speed of said stem in said cylinder.

2. Prosthesis, according to claim 1, characterised in that a force transducer is provided in said damper, and the microprocessor receives a force signal from said force transducer and adjusts the damping reaction of said damper responsive to the force signal from said damper.

3. Prosthesis, according to claim 2, characterised in that said force transducer is provided in said stem, and the microprocessor receives a force signal from said transducer on the stem and adjusts the damping reaction of said damper responsive to the detected force signal on the stem.

4. Prosthesis, according to claim 2, characterised in that said force transducer is a ring dynamometer, in particular a Morehouse ring, put in a hole made in said stem, with axis of the hole orthogonal to the axis of the stem.

5. Prosthesis, according to claim 2, characterised in that said force transducer on the damper is a load cell arranged at said lower hinge of said damper.

6. Prosthesis, according to claim 2, wherein a force transducer is provided in said femoral segment, selected from the group comprised of: an orthogonal force transducer, a longitudinal force transducer, a torque transducer, or a combination thereof, and said microprocessor receives a force signal from said force transducer in the femoral segment and adjusts the reaction of said damper responsive to the force signal present on said femoral segment.

7. Prosthesis, according to claim 2, wherein a further force transducer is arranged to detect a situation of singularity in flexion by measuring the presence of overloads in bending.

8. Prosthesis, according to claim 6, wherein a memory unit is provided for memorizing the force data of said force transducers, and means for comparing them with maximum admissible values.

9. Prosthesis, according to claim 2, wherein a position transducer is provided at the articulation axis that reproduces the knee movements, said position transducer measuring the rotation of the knee.

* * * * *